US008119152B2

(12) United States Patent
Shikinami

(10) Patent No.: US 8,119,152 B2
(45) Date of Patent: Feb. 21, 2012

(54) IMPLANT MATERIAL AND PROCESS FOR PRODUCING THE SAME

(75) Inventor: Yasuo Shikinami, Osaka (JP)

(73) Assignee: Takiron Co., Ltd., Osaka (JP)

( * ) Notice: Subject to any disclaimer, the term of this patent is extended or adjusted under 35 U.S.C. 154(b) by 1558 days.

(21) Appl. No.: 10/496,076

(22) PCT Filed: Nov. 20, 2002

(86) PCT No.: PCT/JP02/12130
§ 371 (c)(1),
(2), (4) Date: May 20, 2004

(87) PCT Pub. No.: WO03/045460
PCT Pub. Date: Jun. 5, 2003

(65) Prior Publication Data
US 2004/0258732 A1    Dec. 23, 2004

(30) Foreign Application Priority Data

| Nov. 27, 2001 | (JP) | ............................. P. 2001-360766 |
| Dec. 3, 2001 | (JP) | ............................. P. 2001-368558 |
| Feb. 20, 2002 | (JP) | ............................. P. 2002-043137 |
| Aug. 23, 2002 | (JP) | ............................. P. 2002-242800 |
| Sep. 30, 2002 | (JP) | ............................. P. 2002-285933 |
| Sep. 30, 2002 | (JP) | ............................. P. 2002-285934 |

(51) Int. Cl.
*A61F 2/00* (2006.01)
(52) U.S. Cl. ........................................ 424/424
(58) Field of Classification Search ................ 424/423, 424/425, 426; 428/36.1, 36.3
See application file for complete search history.

(56) References Cited

U.S. PATENT DOCUMENTS

| 5,624,463 | A | | 4/1997 | Stone et al. |
| 5,711,960 | A | * | 1/1998 | Shikinami ..................... 424/426 |
| 5,981,619 | A | | 11/1999 | Shikinami et al. |
| 6,203,574 | B1 | * | 3/2001 | Kawamura ................. 623/16.11 |
| 2001/0021530 | A1 | * | 9/2001 | de Bruijn et al. ............. 435/395 |
| 2001/0031254 | A1 | | 10/2001 | Bianchi et al. |

FOREIGN PATENT DOCUMENTS

| EP | 277678 A | 8/1988 |
| EP | 677297 A | 10/1995 |
| JP | 60-126359 A | 7/1985 |
| JP | 63-272355 A | 11/1988 |
| JP | 1-501208 A | 4/1989 |
| JP | 1501208 A | 4/1989 |
| JP | 02-215461 A | 8/1990 |
| JP | 6-38936 U | 5/1994 |
| JP | 07-148243 A | 6/1995 |
| JP | 8-299280 * | 9/1996 |
| JP | 9-182784 A | 7/1997 |
| JP | 10-33656 A | 2/1998 |
| JP | 10-52485 A | 2/1998 |
| JP | 10-179715 A | 7/1998 |
| JP | 11290447 A | 10/1999 |
| JP | 2003-33429 A | 2/2003 |
| WO | 88/01517 A1 | 3/1988 |
| WO | WO 88/01517 A1 | 3/1988 |
| WO | WO 88/03417 A1 | 5/1988 |
| WO | WO 00/13717 A1 | 3/2000 |
| WO | WO 00/21470 A | 4/2000 |
| WO | WO 01/39680 A1 | 6/2001 |
| WO | 01 85226 * | 11/2001 |
| WO | 0203895 A1 | 1/2002 |

OTHER PUBLICATIONS

International Search Report, dated Mar. 11, 2003.
Japanese Office Action dated Jun. 20, 2007.
Japanese Office Action dated Oct. 28, 2008.
Japanese Office Action for JP Application No. 2001-360766 dated Dec. 28, 2007.
Japanese Office Action for JP Application No. 2002-043137 dated Dec. 14, 2007.
Australian Office Action issued in Application No. 2007-229341, dated Sep. 25, 2009.
Devin, J., et al., "Three-dimensional degradable porous polymer-ceramic matrices for use in bone repair", Journal of Biomaterials Sciences Polymer Edition, vol. 7, No. 8, 1996, pp. 661-669, VSP, Utrecht, Netherlands, XP 001057150.
Supplementary European Search Report issued Mar. 15, 2010 in a counterpart European Application No. 02788632.4.
Office Action issued on Mar. 25, 2010 in counterpart Norwegian Application No. 20042189.

* cited by examiner

*Primary Examiner* — Tracy Vivlemore
*Assistant Examiner* — Jennifer Berrios
(74) *Attorney, Agent, or Firm* — Roylance, Abrams, Berdo & Goodman, L.L.P.

(57) ABSTRACT

The present invention provides an implant material comprising an organic-inorganic complex porous article and a production method thereof. The organic-inorganic complex porous article is a biodegradable and bioabsorbable bioactive porous article in which a bioactive bioceramics powder is uniformly dispersed in a biodegradable and bioabsorbable polymer, wherein it has continuous pores and the bioceramics powder is partly exposed to the pore inner surface or the pore inner surface and the porous article surface.

14 Claims, 11 Drawing Sheets

IMPLANT MATERIAL AND PROCESS FOR PRODUCING THE SAME

TECHNICAL FIELD

This invention relates to an implant material comprising a bioactive and degradable and absorbable organic-inorganic complex porous article and a production method thereof, and an implant material comprising this complex porous article and other biomaterial.

BACKGROUND OF THE INVENTION

As inorganic porous articles to be used for clinical purposes, for example, porous ceramics obtained by calcining or sintering bioceramics are known. However, since such porous ceramics show a disadvantage of being hard but friable when used in applications such as a scaffolding for living bone tissue reconstruction, a prosthetic material and the like, there always is a danger of causing destruction by a slight impact after the operation. Also, it is difficult to process and change the shape of porous ceramics to match to the shape of the damaged part of a living bone tissue in the field of operation, too. In addition, since 10 years or more of a prolonged period of time is required in some cases until it is completely replaced by a living bone, a danger of causing harmful effects by its destruction remains during this period.

On the other hand, as organic porous articles to be used for clinical purposes, for example, a sponge and the like disclosed in JP-B-63-64988 are known. This sponge is generally used for the blood stanching at the time of surgical operation or as a prosthetic material at the time of the suture of a soft tissue (e.g., an organ) in the living body, which is a sponge having continuous pores comprising a biodegradable and bioabsorbable polylactic acid. Such a sponge is produced by a method in which polylactic acid is dissolved in benzene or dioxane, and the solvent is sublimed by freeze-drying the polymer solution.

However, regarding a porous article produced by a freeze drying method such as the case of the above sponge, it is difficult to remove the solvent completely because it requires a prolonged period of time for the sublimation, and since it has a thin thickness of 1 mm or less (generally about several hundred μm), it is difficult in reality to produce a porous article having a thickness of several mm or more. As other methods for producing porous articles having continuous pores, various methods have been examined in addition to the aforementioned freeze drying method, but it is not easy to obtain a thick porous article of several mm or more. It is impossible to apply such a thin porous article in compliance with the shape of, for example, a complex and relatively large three dimensional space of a damaged part of a living body tissue, thereby allowing it to exert its function as a temporal prosthetic material and simultaneously effecting three dimensional tissue reconstruction of the damaged part. Accordingly, there is a demand for those which has thickness, and can be made into a three dimensional cube before or during an operation, and are degraded and absorbed and replaced by a living bone at a relatively early stage.

Also, an elution method is known as another reliable method for making a porous article having continuous pores, in which a large amount of a water-soluble powder having a certain size such as NaCl is mixed with a polymer, and the mixture is formed into a sheet or the like thin molding and then soaked in water (solvent) to effect elusion of said powder, thereby forming continuous pores having the same diameter of said powder, but since it is difficult to elute said powder completely, the products are limited to thin article of continuous pores. Also, continuous pores can hardly be obtained when ratio of the water-soluble powder becomes high. What is more, when this porous article is embedded into the living body, it causes a problem of being encumbered with the toxicity of said powder still remaining.

Like the case of the aforementioned sponge, a porous article which does not contain bioactive bioceramics and the like inorganic powders is lacking direct bindability, conductivity, replaceability and the like with bone, cartilage and the like bone tissues in the living body, so that not osteoblast but fibroblast and the like soft tissues are penetrated and present therein, thus requiring a considerably prolonged period of time until the bone tissue in the living body is completely replaced and regenerated, or it ends up un-replaced.

Accordingly, the present applicant has already applied for a patent on a thick porous article having continuous pores comprising a biodegradable and bioabsorbable polymer, wherein a bioactive bioceramics powder is contained inside thereof, which becomes a scaffold of a three dimensional cube when osteoblast is inoculated and can be transplanted into a damaged part of a large bone for mediation (Japanese Patent Application No. 8-229280).

This porous article is produced by a porous article production method called solution precipitation method. That is, by a method in which a suspension is prepared by dissolving a biodegradable and bioabsorbable polymer in a mixed solvent of its solvent with a non-solvent having a boiling point higher than that of the solvent and simultaneously dispersing a bioceramics powder therein, and the bioceramics powder-including biodegradable and bioabsorbable polymer is precipitated by evaporating the mixed solvent from this suspension at a temperature lower than the boiling point of the solvent.

The principle for forming a porous article by this solution precipitation method is as follows. That is, when the mixed solvent is evaporated from the aforementioned suspension at a temperature lower than the boiling point of the solvent, ratio of the non-solvent having higher boiling point is gradually increased by preferential evaporation of the solvent having lower boiling point, and the solvent becomes unable to dissolve the polymer when the solvent and non-solvent reach a certain ratio. Because of this, the polymer starts its deposition and precipitation and includes the bioceramics powder which is starting its precipitation from the beginning, the thus deposited and precipitated polymer is shrunk and solidified by the high ratio non-solvent and fixed while including the bioceramics powder, and a cell structure in which the mixed solvent is included is formed on the connected thin cell walls of the polymer. Thereafter, the remaining solvent evaporates and disappears while making pores by destroying parts of the cell walls, and the non-solvent having higher boiling point also evaporates gradually through said pores and completely evaporates and disappears in the end. As a result, a bioceramics powder-containing porous article is formed, in which remains of the mixed solvent reservoirs included in the polymer cell walls are connected as continuous pores.

The aforementioned solution precipitation method is an epoch-making method which can form a thick porous article having from a low expansion ratio to a high expansion ratio, and it is possible to obtain a block-shaped three dimensional porous article having a thickness of from several mm to several ten mm. Accordingly, this is markedly useful for, e.g., a scaffold of the regeneration of a solid shape (three dimensional solid shape) bone having large relief.

However, this method has a disadvantage in that a bioceramics powder belonging to a relatively large particle diameter among the particle diameter distribution in a suspension containing the bioceramics powder in a large amount starts its precipitation from the beginning of the solvent evaporation, and a fairly large amount of the bioceramics powder is already starting its precipitation with a density gradient toward the bottom when the polymer starts its deposition and precipitation, so that the bioceramics powder content of the thus obtained porous article is not uniform as a whole and it is not avoidable therefore that the content increases from the upper side toward the bottom side of the porous article. Such a heterogeneous porous article having a density gradient of the content cannot be used efficiently and indiscriminately for its applications such as a scaffold for bone tissue reconstruction, a prosthetic material, a bone filler and the like. It is possible to improve such a problem to a certain degree by controlling sedimentation velocity and the like of the bioceramics powder by a certain method, but it cannot be solved completely. Particularly, it is difficult, not only by the invention but in general, to prepare a porous article for three dimensional bone reconstruction use containing 30% by weight or more of a bioceramics powder and having a homogeneous and uniform concentration.

Regarding the porous article having a small content of bioceramics powder produced by the aforementioned method, the majority of the bioceramics powder is included in the polymer cell wall and can hardly be exposed to the inner face of the continuous pores and the surface of the porous article, so that it has a problem in that when embedded in the living body, conduction action of a living bone tissue by the bioceramics powder can hardly be exerted from just after the embedding, and the bioactivity therefore is exhibited having a time lag together with the bioceramics powder exposed at the same time with the degradation of the polymer which forms a skin layer.

Also, even when extremely fine particles are selected as the bioceramics powder, its percentage content in the porous article produced by the aforementioned method is up to about 30% by weight at the most, and when it is contained in an amount larger than this, the bioceramics powder becomes more apt to precipitate so that the bottom side of the thus obtained porous article contains a large amount of the bioceramics powder and therefore becomes extremely brittle.

In addition, the porous article produced by the aforementioned method generally has continuous pores in a large occupying ratio of 80% or more, but in generally saying, only continuous pores having a relatively small pore diameter of from several μm to several ten μm are obtained so that it cannot always say that the pore diameter and pore shape ideal for the penetration and proliferation of osteoblast into and in the porous article are formed.

Methods for highly filling inorganic powder substances have been examined by other methods than the aforementioned solution precipitation method of the present applicant, and one of the influential methods among them is a method for preparing an article of continuous pores by a baking method in which granules are prepared by filling a polymer with about 50% by weight of a bioceramics powder, and these particles are fused on the surface by heating. This method is not a brand-new method but well known as a method for preparing a porous article of a granular resin such as an epoxy resin, a vinyl chloride resin or the like. Since this method requires surface fusion, the filling amount has a limitation and 50% by weight or more of filing is hard to achieve due to generation of brittleness, and control of the pore diameter is not easy too, so that a product having good quality can hardly be obtained.

The invention aims at providing various implant materials comprising an organic-inorganic complex porous article highly filled with inorganic particles, which can resolve all of these problems, and production methods thereof. In addition, it also contemplates providing implant materials comprising combinations of this organic-inorganic complex porous article with other living body materials, which are used as bone fixing materials, used as vertebral body fixing materials [intervertebral installation material and vertebral body prosthetic material] and the like, used as substitutes for bone allograft, bone autograft, cortical bone, spongy bone or combinations thereof, used as prosthetic and filling materials and the like for defect parts and deformed parts of bones, used as scaffolds for bone and cartilage formation, and used as artificial cartilage.

Currently, a bone fixing material such as a fixing pin comprising a biodegradable and bioabsorbable polymer is used, which is embedded by bridging the marrow of both sides of an incised part of the sternum, for example, in the surgical operation of sternum splitting incision closing. Since this is gradually degraded and absorbed in the sternum, it has an advantage of not requiring its extraction from the living body by carrying out re-operation like the case of pins made of non-absorbable ceramics or metals, but since it has no bone conduction and does not directly bind to a bone tissue, it merely has an effect to close the incised face through provisional fixing of the closed sternum by exerting an action as a simple "wedge". Because of this, when the spongy bone becomes brittle by changing into a wafer retaining only a thin cortical bone as can be seen in the majority of the sternum of the aged, it causes problems in that even when this fixing pin for the sternum is embedded, it is difficult to increase fixing stability by exerting its action as the "wedge" and it is not replaced by a bone tissue. On the other hand, porous articles of hydroxyapatite (HA) and the like ceramics, which are used for the connection and fixation of cut regions and fractured regions of bones other than the sternum, have problems in that they are apt to break and require a considerably prolonged period of time to be absorbed in the living body. Though there is an opinion that there is no problem even when a prolonged period of time is required, because its strength is restored once embedded in the living bone, but there still is a danger of causing breakage until it is completely embedded. The implant materials of the invention to be used as bone fixing materials mainly aim at resolving these problems.

In this connection, a conventional vertebral body fixing material such as a cage made of titanium or carbon to be used as an intervertebral spacer in the anterior interbody fusion for lumbar spine degeneration diseases satisfies chemical biocompatibility of the surface for the present, but since dynamical biocompatibility is different from the living body, there are problems such as a danger of exhibiting harmful effect on the peripheral tissues by periodical breakage and corrosion due to its protracted presence as a foreign matter in the living body. For example, there is a problem in that the cage subsides into the vertebral body via a osseous endplate exposed by reaming, generated due to disharmony of dynamical characteristics between the cage and the living body. Particularly, being hard but brittle, a cage made of carbon is broken along its carbon fibers and generates fine pieces in some cases, so that a possibility of exhibiting harmful effect thereby always remains. Also, a bone for autograft to be filled in these cages is generally supplied by extracting an ilium, but there are a problem regarding its amount and preparation and a problem in terms of complicated treatments after the extraction (after treatment of the extracted region, and pulverization, filling in the cage, treatment under sterile condition and the like of the ilium). The implant materials of the invention to be used as vertebral body fixing materials mainly aim at resolving these problems.

On the other hand, an operation for making up defect parts of bones is usually carried out in recent years making use of a bone allograft prepared by cutting and processing a cadaveric bone or a bone autograft extracted from a region of a large bone such as the pelvis, a rib or the like. When the bone allograft is in a block shape integrated by providing a cortical bone on the surface of a spongy bone, a cortical bone region of a defect position of a bone can be made up by the cortical bone of said allograft, a spongy bone region of a defect position of a bone can be made up by the spongy bone of said allograft. However, since the bone allograft is prepared by cutting and processing a cadaveric bone, it poses a problem in that it is not easy to provide necessary and sufficient amount of graft bone by obtaining the material cadaveric bones in a large amount, and it also poses a problem in that workable shapes are greatly limited. Also, even in the case of a bone allograft, the transplanted said graft bone is a bone tissue different from its own bone tissue, there is a possibility that it disappears by its spontaneous absorption and its strength becomes insufficient or is reduced, depending on the embedding conditions. In addition to this, it is necessary to carry out a sterilization treatment because it is a cadaveric bone of other person, but since denaturation of the cadaveric bone occurs depending on its conditions, it is necessary to control sufficient sterilization conditions. However, since it is insufficient sometimes, there is a case in which generation of a serious accident extending to death is announced after its embedding. Though such an accident can be avoided by a bone autograft extracted during an operation, it cannot be denied that its amount is insufficient. On the other hand, embedding of implant materials made of hydroxyapatite (HA), tricalcium phosphate (TCP) and the like bioactive ceramics are also carried out at a defect part, but in that case, there is a problem in that a cortical bone region and a spongy bone region of a defect position of a bone are evenly made up by the hard ceramics, and since such ceramics remain semipermanently, it still poses a problem of being not able to reconstruct the defect position of bone by a self bone tissue. Thus, a method for obtaining a substitution for the spongy bone by preparing porous articles of said ceramics is becoming considerably realistic. However, since it is the best ideally that these synthetic artificial bones are replaced by living bones, when they are replaced after a prolonged period of 10 to 20 years, an accident as a physical foreign matter during this period must be feared in sometimes. The implant materials of the invention to be used as substitutes for bone allograft and bone autograft mainly aim at resolving these problems.

In addition, a punching (mesh shape) plate made of titanium or the like metal in which a large number of pores are formed by punching, a punched flat plate or rugged plate comprising a compact article or porous article of baked bioceramics, and the like, are used as conventional prosthetic, filling and coating materials of defect parts and deformed parts of bones. However, since the punching plate made of a metal lacks in physical biocompatibility and remains permanently as a foreign matter in the made-up region, there is a danger of exhibiting harmful effect on the peripheral tissues caused by corrosion, metal ion elution and the like during its long-term embedding, so that there is a problem in that the defect parts cannot be completely replaced at all by a bone tissue. In addition, since the porous article of baked bioceramics is hard but brittle and easily broken, there is a danger of being broken by receiving impact during its use and there is a problem in that it cannot be post-formed during an operation to match the three dimensional shape of the defect part of bone. The implant materials of the invention to be used as prosthetic, filling, coating and the like materials mainly aim at resolving these problems.

In addition, a conventional artificial cartilage, for example, a total replacement type independent artificial intervertebral disk is an artificial intervertebral disk having a so-called sandwich structure in which two metal endplates made of titanium or cobalt-chromium are superposed on both sides (upside and down side) of a core comprising bio-inactive polyethylene or a rubber having biocompatibility, wherein the core portion performs a movement similar to that of the living intervertebral disk depending on the superposing condition of the two sheets of polyethylene and, in the case of a rubber, it is imitated by its elasticity. In order to give effect of its independence by preventing slipping when inserted between vertebral bodies, it is made into a structure in which several horns are projected on the surface of the metal plate so that they are fixed by sticking into concave of the vertebral body. However, since this artificial intervertebral disk has a sandwich structure of materials having different qualities from those of the living body, it has great disadvantages in that abrasion is formed between their interface after repetition of movement, it cannot be said by no means that the movement is the same as that of the living intervertebral disk, and the horns projected from the metal plate not only injure the upper and lower vertebral bodies but also cause still more damages by gradually subsiding and penetrating into the vertebral bodies during its use for a prolonged period of time, so that it cannot be independently fixed by directly binding to the upper and lower vertebral bodies. The implant material of the invention to be used as an artificial cartilage mainly aims at resolving these problems, and by intervening the porous article of the invention between vertebral bodies including the endplate, it also aim at effecting close contact by filling a physical gap with said artificial intervertebral disk, and also at effecting direct bonding with the vertebral body by the bone conduction.

DISCLOSURE OF THE INVENTION

The most basic implant material of the invention comprises an organic-inorganic complex porous article which is a biodegradable and bioabsorbable bioactive porous article in which a bioactive bioceramics powder is uniformly dispersed in a biodegradable and bioabsorbable polymer, wherein it has continuous pores and the bioceramics powder is partly exposed to the pore inner surface or the pore inner surface and the porous article surface. As will be described later, this porous article has a porosity of from 50 to 90%, the continuous pores occupy from 50 to 90% of the total pores, and the continuous pores are controlled at a pore size of approximately from 100 to 400 µm which is suitable for the penetration, proliferation and stabilization of osteoblast. In addition, the bioceramics powder is contained in a large amount of from 60 to 90% by weight, and the porous article has a three dimensional solid shape having a large thickness of from 1 to 50 mm. This basic implant material is used in various clinical applications such as a scaffolding for substitution type bone tissue regeneration, a prosthetic material, a coating material, a bone filler, a substitute for spongy bone, an inclusion between a bone tissue and other artificial implant, a drug carrier and the like.

In addition, an implant material comprising an organic-inorganic complex which is a biodegradable and bioabsorbable bioactive porous article in which a bioactive bioceramics powder is uniformly dispersed in a biodegradable and bioabsorbable polymer, wherein it has continuous pores and a bioceramics powder percentage content of from 60 to 90% by weight, is also a basic implant material of the invention and used in various clinical applications similar to the above.

The above implant material comprising an organic-inorganic complex porous article can be produced by a production method of the invention, namely a method in which a nonwoven fabric-like fiber aggregate is formed from a mixed solution prepared by dissolving a biodegradable and bioabsorbable polymer in a volatile solvent and dispersing a bioactive bioceramics powder therein, this is formed into a porous fiber aggregate molding by compression-molding it under heating, the fiber aggregate molding is soaked in the volatile solvent, and then said solvent is removed.

On the other hand, the implant materials of the invention to which the aforementioned organic-inorganic complex porous article is applied are obtained by uniting the aforementioned organic-inorganic complex porous article with other compact biodegradable and bioabsorbable member. The following four kinds are the main types of such implant materials.

The first implant material is an implant material for bone fixation in which the other biodegradable and bioabsorbable member is a pin, wherein said pin is united by penetrating through the aforementioned porous article, and both termini of the pin are stuck out from the aforementioned porous article. This implant material is suitably used, for example, for fixing the sternum split and incised in surgical operation of sternum splitting incision closing.

The second implant material is an implant material in which the other biodegradable and bioabsorbable member is a matrix having a cavity opening into the outside and comprising a biodegradable and bioabsorbable polymer containing a bioactive bioceramics powder, wherein the aforementioned porous article is united by packing in the cavity of said matrix and the aforementioned porous article is partly exposed from said matrix. This implant material is suitably used as an intervertebral spacer or the like vertebral body fixing material in the anterior or posterior interbody fusion and the like.

The third implant material is an implant material in which the other biodegradable and bioabsorbable member is a skin layer comprising a biodegradable and bioabsorbable polymer containing a bioactive bioceramics powder, wherein said skin layer is united by superposing on a part of the surface of the aforementioned porous article in a block shape. In this implant material, the block-shaped porous article takes a role of the spongy bone and the skin layer takes a role of the cortical bone, so that it is suitably used as total absorption substitution type artificial bones such as substitutes for bone allograft, bone autograft and the like.

The fourth implant material is an implant material in which the other biodegradable and bioabsorbable member is a net-shaped body comprising a biodegradable and bioabsorbable polymer containing a bioactive bioceramics powder, wherein the aforementioned porous article is united by packing in the mesh of said net-shaped body. This implant material is suitably used as a prosthetic, coating, supporting or filling material and the like of defect parts and deformed parts of bones.

In addition, still another implant material of the invention applied with the aforementioned porous article is an implant material for artificial cartilage, in which the aforementioned porous article is united by laminating the aforementioned porous article on at least one side of a core material comprising a texture structure body prepared by converting organic fibers into a multi-axial three dimensional weave texture or knit texture of three axes or more or a complex texture thereof. This implant material is suitably used as artificial intervertebral disk, meniscus and the like which are independently fixed by directly binding to the upper and lower vertebral bodies.

BEST MODE FOR CARRYING OUT THE INVENTION

Figure 1:
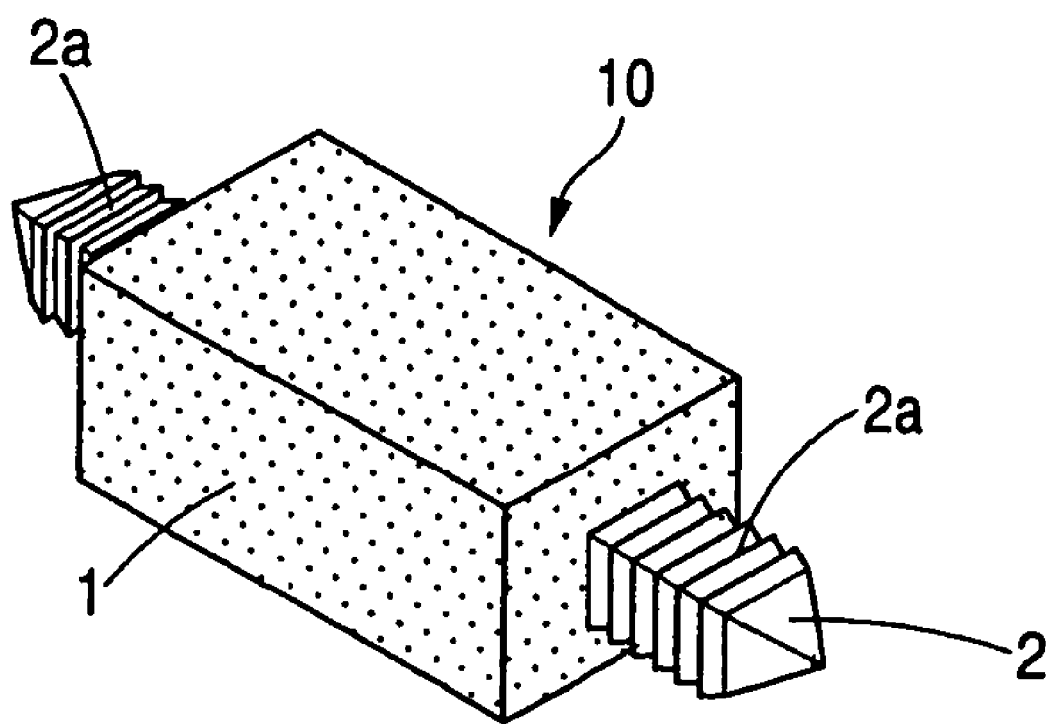
FIG. 1 is a perspective illustration showing an embodiment of the implant material according to the invention.

The following illustratively describes desirable embodiments of the implant materials of the invention and production methods thereof.

The most basic implant material of the invention comprises an organic-inorganic complex porous article which is a biodegradable and bioabsorbable bioactive porous article in which a bioactive bioceramics powder is uniformly dispersed in a biodegradable and bioabsorbable polymer, wherein it has continuous pores and the bioceramics powder is partly exposed to the pore inner surface or the pore inner surface and the porous article surface, and in its desirable embodiment, a polymer which is already put into practical use by confirming its safety, degraded relatively quickly and not brittle when the porous article is formed is selected and used as the biodegradable and bioabsorbable polymer. That is, amorphous or crystalline/amorphous-mixed totally absorbable poly-D,L-lactic acid, a block copolymer of L-lactic acid with D,L-lactic acid, a copolymer of lactic acid with glycolic acid, a copolymer of lactic acid with p-dioxanone, a copolymer of lactic acid with ethylene glycol, a copolymer of lactic acid with caprolactone, a mixture thereof and the like biodegradable and bioabsorbable polymers are used. A polymer having a viscosity average molecular weight of from 50,000 to 1,000,000 is preferably used by taking into consideration easy formation of the nonwoven fabric-like fiber aggregate in the production method of the invention and period of degradation and absorption of the porous article in the living body.

Particularly, poly-D,L-lactic acid, a block copolymer of L-lactic acid with D,L-lactic acid, a copolymer of lactic acid with glycolic acid, a copolymer of lactic acid with p-dioxanone and the like biodegradable and bioabsorbable polymers which show amorphous nature based on the monomer ratio are desirable from the viewpoint of solvent characteristics when a nonwoven fabric-like fiber aggregate is formed in accordance with the production method of the invention and when a porous fiber aggregate molding formed by compression-molding this under heating is treated with a volatile solvent, and the use of these polymers renders possible preparation of an implant material comprising an organic-inorganic complex porous article, which is not brittle even when a large amount of bioceramics powder is contained, has a compressive strength equivalent to that of spongy bone, can be heat-deformed at a relatively low temperature (about 70° C.) different from the case of porous articles of ceramics alone, and is quickly hydrolyzed and completely absorbed after 6 to 12 months in the living body. An implant material having such characteristics is markedly desirable as a material for filling a defect part of a living bone, and being a complex body, it also maintains thermoplastic resin-specific advantages in that it maintains viscoelasticity by the resin component different from the case of a material of ceramics alone, it does not cause breakage unlike the case of ceramics due to brittleness when merely touched, and its shape can be adjusted to match with a defect part during an operation by heat-deforming it.

Since molecular weight of a biodegradable and completely bioabsorbable polymer exerts influence upon the period until it is hydrolyzed and completely absorbed and the possibility of fiber formation, a polymer having a viscosity average molecular weight of from 50,000 to 1,000,000 is used as described in the foregoing. A polymer having a viscosity average molecular weight of smaller than 50,000 has a short period of time until hydrolyzed into an oligomer or monomer unit having low molecular weight, but being insufficient in spinnability, it is difficult to form a fiber aggregate while forming fibers by spraying or the like means in accordance with the production method of the invention. Also, a polymer having a viscosity average molecular weight of larger than 1,000,000 requires a long period of time until completely hydrolyzed, so that it is unfit for the polymer of complex porous articles when early stage replacement by a living bone tissue is the object. Though it varies depending on each polymer, its desirable viscosity average molecular weight is from 100,000 to 300,000, and when a biodegradable and bioabsorbable polymer having a molecular weight within this range is used, formation of the fiber aggregate becomes easy, and an implant material of complex porous article having appropriate hydrolysis complete period can be obtained.

Also, in the implant material comprising an organic-inorganic complex porous article, a powder having a bioactivity and good bone conduction (occasionally showing bone induction) and good biocompatibility is used as the bioceramics powder to be dispersed in the porous article. Examples of such a bioceramics powder include powders of calcined or sintered hydroxyapatite, apatite wollastonite glass ceramics, bioactive and completely bioabsorbable un-calcined or un-sintered hydroxyapatite, dicalcium phosphate, tricalcium phosphate, tetracalcium phosphate, octacalcium phosphate, calcite, ceravital, diopside, natural coral and the like. In addition, those which are prepared by adhering an alkaline inorganic compound, a basic organic compound and the like on the surface of these powders can also be used. Because of the reason that tissue regeneration carried out by total substitution by a self bone tissue is ideal, a completely bioabsorbable bioceramics powder which is completely absorbed and completely replaced by a bone tissue in the living body is desirable among them, and un-calcined or un-sintered hydroxyapatite, tricalcium phosphate and octacalcium phosphate are particularly desirable because they have large activities, are excellent in bone conduction, have low harmful effect due to excellent biocompatibility and are absorbed in the living body during a short period of time.

It is desirable to use the aforementioned bioceramics powder having an average particle size (average particle size of primary particles) of from 0.2 to 10 μm, because when a bioceramics powder having a particle size larger than this is used, it becomes difficult to form a fiber aggregate due to cutting of fibers into short pieces when a mixed solution prepared by mixing said powder is splayed and made into fibers by the production method of the invention, and even in case that a fiber aggregate can be formed, there is a possibility that the bioceramics powder is slightly precipitated and dispersed unevenly before the fibers are solidified. Those having a size exceeding 20 to 30 μm are not desirable, because even they are completely absorbable, a prolonged period of time is required for their complete absorption, and tissue reactions during that period are exhibited occasionally.

More preferred particle size of bioceramics powder is from 0.2 to 5 μm, because when such a bioceramics powder is used, fibers are hardly cut out in case that a fiber aggregate is formed by making a mixed solution prepared by mixing high concentration of said powder in the production method of the invention into fine fibers having a fiber diameter of from 1 to 3 μm, and when it is in a high concentration like the case of the invention, said powder is included in fibers under a condition of being exposed from the fibers so that the fiber aggregate after its soaking treatment with a volatile solvent becomes a complex porous article in which said powder is exposed from the surface or inner surface of the continuous pores.

In the case of an implant material comprising an organic-inorganic complex porous article, which is used for clinical applications such as a scaffold in regeneration medical engineering, a carrier or bone filler for DDS, a substitute for a heteromorphic spongy bone (bone allograft) and the like, it is desirable to control percentage content of the bioceramics powder within the range of from 60 to 90% by weight from the viewpoint of bioactivity of the bioceramics. When a complex porous article is prepared by forming an aggregate of fibers containing a bioceramics powder and soaking, in a volatile solvent, a fiber aggregate molding prepared by compression-molding under heating, like the case of the production method of the invention, a large amount of the bioceramics powder can be contained within such a range that it is possible to form fibers, so that percentage content of the bioceramics powder can be increased to a level of from 60 to 90% by weight (volume % when a powder having an average particle size of 3 μm and a specific gravity of 2.7 is used corresponds to a high ratio of approximately from 41 to 81%) as described in the above. In case that the percentage content of bioceramics powder exceeds 90% by weight, formation of a fiber aggregate becomes difficult because satisfactory fibers cannot be obtained due to their cutting into short pieces when fiber formation is carried out, and when it is less than 60% by weight on the other hand, the bioceramics powder is insufficient and hardly exposed to the surface, so that the bioactivity originated from the bioceramics powder is hardly exhibited from the early stage after embedding of the implant material into the living body.

Such a complex porous article which enabled to uniformly disperse a bioactive bioceramics powder in a high percentage content of from 60 to 90% by weight in this manner cannot be found in the prior art and is one of the basic implant materials of the invention.

Desirable volume % of the bioceramics powder is from 50 to 85% by volume. This volume % is a percentage of the volume of the bioceramics powder to the volume of the polymer in case that porosity of the polymer in the complex porous article is 0%, and the volume % changes depending on the specific gravity and average particle size of the bioceramics powder even when weight of the bioceramics powder is constant. Accordingly, taking specific gravity and average particle size of the bioceramics powder into consideration, it is desirable to contain it at from 50 to 85% by volume. More desirable volume % is from 50 to 80% by volume.

Since porous ceramics obtained by sintering hydroxyapatite and the like ceramics are hard but brittle, thin materials are easily broken or chipped by an external force and not satisfactory as implants. Contrary to this, a complex porous article prepared by including a bioceramics powder particularly in an amorphous biodegradable and bioabsorbable polymer has a compressive strength equivalent to that of the spongy bone which keeps flexibility and is not brittle, illustratively a compressive strength of approximately from 1 MPa to 5 MPa, by the binding effect of the polymer even when the bioceramics powder has a high percent content of from 60 to 90% by weight, so that it can be suitably used for a substitute for spongy bone and other clinical applications as has been already described. In this connection, the aforementioned compressive strength is a value measured using an autograph AGS-2000D manufactured by Shimadzu, based on the test method of JIS K 7181 (however, the size of each sample was fixed to 10×10×15 mm, and the compression speed to 5 mm/min).

An implant material comprising this organic-inorganic complex porous article has a porosity (total porosity) of 50% or more, which can be increased to about 90% technically, but when both of the physical strength of this complex porous article and penetration and stabilization of osteoblast are taken into consideration, it is approximately from 60 to 80%, and when the penetrating efficiency of osteoblast into the central part of the complex porous article is taken into consideration, it is desirable that the continuous pores occupy 50 to 90%, particularly 70 to 90%, of the total pores.

Pore size of the continuous pores of this organic-inorganic complex porous article is set to approximately from 100 to 400 μm. Studies on the pore size of porous ceramics and penetration and stabilization of osteoblast have already been carried out many times, and it has been revealed based on the results that a pore size of from 300 to 400 μm is most effective for calcification and the effect is diluted as departing from this range. Thus, though the pore size of this complex porous article is set to a value of approximately from 100 to 400 μm as described in the foregoing, those having a pore size within the range of from 50 to 500 μm are included, and the distribution center may be from 200 to 400 μm.

In this connection, when pore size of the continuous pores is larger than 400 μm and porosity (total porosity) is higher than 90%, strength of the complex porous article is reduced so that it is highly possible to cause its breakage during embedding in the living body. On the other hand, when the pore size is smaller than 100 μm and the porosity is lower than 50%, strength of the complex porous article is improved but the period until its hydrolysis and complete absorption is prolonged because penetration of osteoblast becomes difficult. However, such a low porosity complex porous article having small pore size can be used in some cases as a material from which retaining of sustained release property is required for a relatively prolonged period of time in parallel with the degradation of the polymer as a carrier of DDS. More preferred pore size of the continuous pores is from 150 to 350 μm, and more preferred porosity (total porosity) is from 70 to 80%. In this connection, the pore-size of continuous pores and the ratio of continuous pores occupying total pores can be controlled by adjusting the compressibility when a fiber aggregate is formed into a fiber aggregate molding by its compression molding in the production method of the invention or by adjusting the external pressure for shape-keeping when the fiber aggregate molding is soaked in a volatile solvent while keeping its shape.

The aforementioned implant material comprising an organic-inorganic complex porous article is used, for example, by embedding it into a defect part of a living bone, and in that case, the implant material can be embedded without a gap in the defect part by deforming it into a shape matching the defect part through its heating at about 70° C. making use of thermoplastic property of the biodegradable and bioabsorbable polymer, so that it becomes possible to carry out the embedding operation simply and accurately. In addition, due to the toughness possessed by the biodegradable and bioabsorbable polymer and the hardness of ceramics powder, it is possible to use it by cutting into an optional shape without loosing the shape using a surgical knife during an operation.

When an implant material comprising this complex porous article is embedded into a defect part of a living bone as described in the above, humor are quickly permeated into inside of the complex porous article from the surface of the complex porous article through the inside of continuous pores, so that hydrolysis of the biodegradable and bioabsorbable polymer progresses almost simultaneously from both of the surface of the complex porous article and the inside of the continuous pores, and the degradation progresses uniformly over the entire porous article. In addition, due to the bone conduction ability of the bioceramics powder exposing on the surface of the complex porous article, a bone tissue is quickly conducted and formed on the surface layer of the complex porous article and grows as a small column of bone, and the complex porous article binds to the defect part of living bone within a short period of time, and also due to the bone conduction ability of the bioceramics powder exposing inside of the pores, the bone tissue penetrates also into inside of the complex porous article and effect conduction and growth of osteoblast so that it directly binds to the peripheral bone. This phenomenon becomes significant accompanied by the progress of degradation of the biodegradable and bioabsorbable polymer, and it is gradually substituted with the peripheral bone. Finally, the polymer is completely degraded and absorbed and the completely absorbable bioceramics powder is also completely absorbed, and regeneration of the defect part of bone is completed through complete replacement by the grown bone tissue.

Wettability of this implant material comprising the complex porous article in the living body is considerably improved than that of a porous article of a biodegradable and bioabsorbable polymer alone, due to the wettability of the bioceramics powder contained in a large amount and exposed on the surface, but wettability of the polymer is also improved when corona discharge, plasma treatment, hydrogen peroxide treatment or the like oxidation treatment is applied to this complex porous article, so that penetration and growth of the osteoblast to be proliferated can be carried out further effectively.

In addition, when various types of ossification factors, growth factors, drugs and the like are included by filling them in pores of the complex porous article in advance or dissolving in the biodegradable and bioabsorbable polymer in advance, they are gradually released in response to the degrading and absorbing rate of the complex porous article, so that regeneration of bones and healing of diseases can be accelerated and effected. The main ossification factor includes BMP, and examples of the main growth factors include IL-1, TNF-α, TNF-β, IFN-γ and the like monokine and lymphokine, or colony-stimulating factor, or TGF-α, TGF-β, IGF-1, PDGF, FGF and the like so-called proliferation differentiation factors. Also, drugs which are concerned in the growth of bones (vitamin D, prostaglandins, anti-tumor (carcinostatic) agents and the like), antimicrobial agents and the like can be optionally selected as the drugs.

Next, the method of the invention for producing an implant material comprising an organic-inorganic complex porous article is illustratively described in detail.

According to the production method of the invention, the aforementioned biodegradable and bioabsorbable polymer is dissolved in a volatile solvent, and a mixed solution is prepared by uniformly dispersing the aforementioned bioceramics powder therein. As the volatile solvent, dichloromethane, dichloroethane, methylene chloride, chloroform or the like low boiling point solvent which is apt to evaporate at a temperature slightly higher than the ordinary temperature can be used. It is also possible to use are volatile mixed solvents prepared by mixing these solvents with one or two or more of non-solvents having boiling points higher than these solvents, such as methanol, ethanol, 1-propanol, 2-propanol, 2-butanol, ter-butanol, ter-pentanol and the like alcohols having a boiling point within the range of from 60 to 110° C.

Next, a nonwoven fabric-like fiber aggregate is prepared from the above mixed solution. As its means, a means for making fibers by spraying the dissolved mixed solution is preferably used. That is, when the aforementioned dissolved mixed solution is charged in a sprayer and the mixed solution is sprayed to a substance from the injection nozzle of the sprayer with nitrogen gas or the like inert high pressure injection gas, fibers are formed while the volatile solvent is evaporated, and fibers of the biodegradable and bioabsorbable polymer containing the bioceramics powder are aggregated, solidified and accumulated by mutually entwining and adhering at their contacting points, thereby effecting formation of a thick nonwoven fabric-like fiber aggregate of an optional shape. Though shape of the inter-fiber gap is different from a cell-shape pore, this fiber aggregate forms continued spaces of approximately several hundred μm between the adhered and solidified fibers, and the bioceramics powder is included in the fibers (partly exposing on the surface) and uniformly dispersed over all of the fiber aggregate molding.

For the purpose of making such a resin containing a bioceramics powder in a large amount of 60% by weight or more (sometimes 50% volume or more) into a material in which this is fixed by solidifying under a uniformly dispersed state without causing precipitation and separation and it also contains continuous gaps as pores inside thereof, it is reasonable to use a means for evaporating a solvent while forming thin fibers by a spraying system and effecting their solidification within a short period of time before separation of the bioceramics powder, like the case of this production method, and a novelty of the production method of the invention also resides therein.

In this connection, in order to obtain a complex porous article having an extremely thick thickness of from 5 to 50 mm which is necessary sometimes as an implant material for clinical use, a predetermined thickness may be obtained by forming this fiber aggregate by spraying and then, after its drying by evaporation of the solvent, again repeating a step of thickening it by spraying thereon.

As the aforementioned substance to be injected, a net or plate comprising a polyethylene or the like olefinic resin, a fluorine resin, a silicon resin or the like having good releasing ability is used. Particularly, when a net or the like substance to be injected having free aeration is used, the mixed solution is formed into fibers by its spraying and hit the net and then the volatile solvent is evaporated through the mesh, so that it has advantages in that a fiber aggregate can be formed without generating a skin layer (adhered layer of the resin alone) by fusion of fibers on the surface of the net side, and a permeation treatment of the solvent in the subsequent step can be easily carried out. A net having a mesh of from 50 to 300 is desirable, because a net having a mesh of larger than 50 meshes causes turning of fibers into the backside through the mesh and therefore entails in a difficulty in releasing the formed fiber aggregate from the net, and a net having a mesh of smaller than 300 meshes cannot perform smooth evaporation of the volatile solvent so that the net side fibers are apt to fuse and form a skin layer. In this connection, the substance to be injected is not limited to a flat net or plate, and a convex-curved and/or concave-curved three dimensional net or plate may also be used. The use of such a three dimensional substance to be injected has an advantage in that a fiber aggregate having a thickness identical to the three dimensional shape can be formed.

The fiber aggregate formed by making fibers by spraying the mixed solution as described in the above has a large inter-fiber gap of several hundred μm, and the ratio of inter-fiber gaps (porosity) is approximately from 60 to 90%. In addition, since the inorganic particles are contained in fibers and do not precipitate, they are uniformly dispersed over entire part of the fiber aggregate.

It is desirable that the fiber length of this fiber aggregate is approximately from 3 to 100 mm, and it is desirable that the fiber diameter is approximately from 0.5 to 50 μm. A fiber aggregate having such degrees of fiber length and fiber diameter is convenient for obtaining a complex porous article from which fibers are substantially disappeared through easy fusion of the fibers by the subsequent step for permeation treatment of the solvent.

The fiber length mainly depends on the molecular weight of the biodegradable and bioabsorbable polymer, polymer concentration of the mixed solution, percentage content and particle size of the bioceramics powder and the like, and there is a tendency that the fiber length becomes long as the molecular weight becomes large, the polymer concentration becomes high, the percent content of bioceramics powder becomes small and the particle size of bioceramics powder becomes small. On the other hand, the fiber diameter mainly depends on the polymer concentration of the mixed solution, percentage content of the bioceramics powder, size of the injection nozzle of the sprayer and the like, and there is a tendency that the fiber diameter becomes thick as the polymer concentration becomes high, the percentage content of bioceramics powder becomes large, and the size of injection nozzle becomes large. In addition, the fiber diameter is also changed by the pressure of injection gas. Accordingly, in order to obtain the aforementioned fiber length and fiber diameter, it is necessary to control molecular weight of the polymer, polymer concentration, percentage content and particle size of the bioceramics powder, size of the injection nozzle, gas pressure and the like.

Next, a subsequent step is carried out for forming a porous fiber aggregate molding by compression-molding the aforementioned fiber aggregate under heating. Firstly, preliminary moldings having continued voids are prepared by solidifying the fiber aggregate under heating and compression, and the preliminary moldings are subjected to compression molding under higher pressure than the former, thereby obtaining a porous fiber aggregate molding having a strength and controlled ratio of continued voids and pore size. In this case, the heating at the time of compression molding is such a degree that the fiber aggregate is slightly softened, and the compression is controlled at such a degree that porosity of the finally obtained complex porous article becomes from 50 to 90% and pore size of the continuous pores becomes roughly from 100 to 400 µm.

By further moving to the next step, the fiber aggregate molding obtained in the previous step is soaked in the aforementioned volatile solvent to effect sufficient permeation of said solvent into inside of the molding. Thereafter, this solvent is removed. When the fiber aggregate molding is soaked in the volatile solvent, the fiber aggregate molding is packed in a mold with a face having a large number of pores and soaked while maintaining the shape under such a condition that an appropriate pressure is added to the fiber aggregate molding from the outside. Alternatively, the solvent may be permeated by pouring it on the upper surface of the fiber aggregate molding. In addition, in order to maintain a desired shape, it is desirable to remove the solvent quickly by a method in which the solvent inside of the fiber aggregate molding is vacuum-suctioned.

When the fiber aggregate molding is soaked in the volatile solvent to allow the solvent to permeate into the molding, the fibers are fused with one another while the fibers contract by dissolving in the solvent from the surface, and the fibers substantially disappear to form a foamed membrane. Thereafter, a foamed wall is formed under such a state that continued round pores having a gap pore size of approximately from 100 to 400 µm are remained, and its shape is changed to a body of continuous pores. A part of the bioceramics powder contained in the fibers in a large amount is included inside of the pore membrane (inside the foamed wall) accompanied by the fusion of fibers and morphological changes by membrane formation, without causing precipitation, and a part thereof is exposed from the pore membrane and also exposed on the porous article surface by embedding in such a degree that said powder does not easily fallout. However, there is a case in which a skin layer is formed on the surface depending on the conditions so that the bioceramics powder is not exposed on the porous article surface, and in that case, a treatment for exposing the inorganic powder present in the surface layer through removal of the skin layer by sanding may be carried out.

In this manner, it is possible to obtain an implant material comprising an organic-inorganic complex porous article having continuous pores, in which a large amount of a bioceramics powder is uniformly dispersed and a part of the bioceramics powder is exposed to the inner side of pores and the porous article surface. According to this complex porous article, the average pore size of continuous pores can be controlled at approximately from 100 to 400 µm which is convenient for the penetration and stabilization of osteoblast, and the porosity can also be controlled at approximately from 50 to 90%, by controlling external pressure for keeping shape of the fiber aggregate molding when it is soaked in the volatile solvent. In this connection, when the soaking treatment of the fiber aggregate molding in the volatile solvent is carried out under heating at from 50 to 60° C., fibers are sufficiently fused with one another by merely allowing the fiber aggregate molding as it is for a short period of time so that the complex porous article can be obtained efficiently.

According to the production method of the invention, it is possible to contain a bioceramics powder uniformly in the complex porous article in an amount of from 60 to 90% by weight (corresponds to 41 to 81% by volume in the case of unbaked hydroxyapatite having an average particle size of 3 µm and a specific gravity of 2.7) within such a range that fibers can be formed, and even when contained in a large amount, the solvent is evaporated and the fibers are adhered before the bioceramics powder is precipitated and separated, so that a high percentage content complex porous article in which the bioceramics powder is uniformly dispersed in comparison with the porous article obtained by the aforementioned solution precipitation method, which could not so far been obtained, can be finally obtained. However, there is an upper limitation, because when the percentage content is too high, amount of the biodegradable and bioabsorbable polymer as a binder becomes small, and the complex porous article becomes brittle and keeping of its shape therefore becomes difficult.

EXAMPLES

Next, further illustrative embodiments of the implant material of the invention comprising an organic-inorganic complex porous article are described.

Example 1

By uniformly homogenizing a polymer solution prepared by dissolving poly-D,L-lactic acid (PDLLA) (molar ratio of D-lactic acid and L-lactic acid, 50/50) having a viscosity average molecular weight of 200,000 in dichloromethane (concentration: PDLLA 4 g/dichloromethane 100 ml) and a suspension prepared by suspending unbaked hydroxyapatite powder (u-HA powder) having an average particle size of 3 µm in ethanol, a mixed solution in which 230 parts by weight of u-HA powder is mixed with 100 parts by weight of PDLLA was prepared.

Using HP-E Air Brush (mfd. by Anest Iwata) as a sprayer, the above suspension was charged into this and sprayed on a polyethylene net (150 mesh) at about 120 cm distance by 1.6 kg/cm² pressure nitrogen gas to form a fiber aggregate, and the fiber aggregate was released from the net. Fiber diameter of this fiber aggregate was about 1.0 µm, its fiber length was approximately from 10 to 20 mm, and its apparent specific gravity was 0.2.

This fiber aggregate was cut into an appropriate size, packed into a cylindrical female die of 30 mm in diameter and 30 mm in depth and compressed with a male die such that apparent specific gravity of the fiber aggregate became 0.5, thereby obtaining a disc shape fiber aggregate molding having a diameter of 30 mm and a thickness of 5 mm.

Next, this fiber aggregate molding was soaked in a solvent comprising ethanol-mixed dichloromethane to effect permeation of said solvent into inside of the molding, and after allowing it to stand at 60° C. for 10 minutes, the solvent in the inner part of the molding was removed by vacuum suction to obtain an organic-inorganic complex porous article having a diameter of 30 mm, a thickness of 4 mm and a u-HA powder percentage content of 70% by weight.

When a partial section of this complex porous article was observed under an electron microscope, the fibers were fused and disappeared, continuous pores having a large pore size of from 100 to 400 μm were formed, the u-HA powder was uniformly dispersed, and a part of the u-HA powder was exposed to the inner face of the pores and the porous article surface. Apparent specific gravity of this complex porous article was 0.5, the ratio of continuous pores occupying total pores (continuous porosity) was 75%, and the compressive strength was 1.1 MPa.

Example 2

A disc shape fiber aggregate molding having a diameter of 30 mm and a thickness of 5 mm was prepared as a preliminary molding in the same manner as in Example 1, and this was heated to 80° C. in a geer oven, put into a chamber equipped with a diameter reducing part in which its diameter is gradually reduced, and then press-fitted into a cylinder having a bottom part diameter of 10.6 mm. The cylindrical rod-shaped fiber aggregate molding compression-molded under heating in this manner showed a compressive strength of about 2.5 MPa.

Next, this cylindrical rod-shaped fiber aggregate molding was put into a cylinder of the same diameter having holes on its periphery and soaked for 10 minutes in a solvent (60° C.) comprising 15% by weight methanol-mixed dichloromethane, while pressing it by applying a pressure from its upper side and lower side to such a degree that height of the cylindrical rod-shaped fiber aggregate molding did not change, and then said solvent was removed to obtain a complex porous article.

When a partial section of this complex porous article and its surface after sanding were observed under an electron microscope, it had a fiber-disappeared porous shape, its pore size was comprised of mixed pores of approximately from 150 to 300 μm, and the u-HA powder was exposed from the porous article surface and the inner face of the pores. Apparent specific gravity of this complex porous article was about 0.55, the continuous porosity was 70%, and the compressive strength was increased to about 3.5 MPa. Judging from the viscosity average molecular weight of PDLLA and the ratio of its occupying amount and the in vivo biodegradable and bioabsorbable characteristics of the u-HA powder having an average particle size of 3 μm, it is considered that this complex porous article is completely absorbed after a period of from about 6 months to 12 months, though it depends on its embedded region and size.

Example 3

A mixed solution was prepared by synthesizing PDLLA (molar ratio of D-lactic acid and L-lactic acid, 30/70) having a viscosity average molecular weight of 100,000 and uniformly mixing it with 80% by weight of a β-tricalcium phosphate powder (β-TCP powder) having an average particle size of about 3 μm by the same method of Example 1. It has been confirmed that this β-TCP powder is bioactive and absorbable in the living body and, though the mechanism is different from the u-HA powder, it is known that this shows a bone conduction ability to form HA in the living body.

Using this mixed solution, a fiber aggregate prepared by the spraying method in the same manner as in Example 2 was made into a fiber aggregate molding by carrying out compression molding under heating, and this was subjected to a solvent soaking treatment to obtain a complex porous article having an apparent specific gravity of about 0.6, a continuous porosity of 75% and a compressive strength of 4.2 MPa. Since volume ratio of the β-TCP powder of this complex porous article is about 65% by volume, the volume ratio of the β-TCP powder is considerably larger than the case of the complex porous articles of Examples 1 and 2 containing 70% by weight (about 55% by volume) of the u-HA powder, so that the bioactivity is significantly exhibited by the exposure of the β-TCP powder to the surface and pore inner face of the porous article.

It was confirmed that, since this complex porous article was changed to a shape due to disappearance of fibers of the nonwoven fabric-like fiber aggregate, in which the β-TCP powder is embedded into the bulky cell walls dispersion of this powder into the peripheral caused by disintegration hardly occurs even when soaked in the humors in the living body, and it is completely degraded and absorbed within 5 to 8 months while showing good bioactivity. Accordingly, this complex porous article becomes a good scaffold for hard tissues (bone and cartilage).

Example 4

D,L-lactic acid (D/L molar ratio, 1) was mixed with glycolic acid (GA) at a molar ratio of 8:2, and a copolymer P (DLLA-GA) having a viscosity average molecular weight of 130,000 was synthesized by a known method. By preparing a mixed solution in which this polymer was uniformly mixed with 60% by weight of an octacalcium phosphate powder (OCP powder), a fiber aggregate prepared by the spraying method in the same manner as in Example 2 was made into a fiber aggregate molding by carrying out compression molding under heating, and this was subjected to a solvent soaking treatment to finally obtain a complex porous article having an apparent specific gravity of 0.50. Since activity of the OCP powder was high and degradation and absorption of the copolymer were quick due to GA, the majority of this complex porous article was absorbed and replaced by a bone after 3 to 4 months showing good bone conduction (aptness to change to a new bone).

Example 5

D,L-lactide was mixed with para-dioxanone (p-DOX) at a molar ratio of 8:2, and a copolymer having a viscosity average molecular weight of about 100,000 was synthesized by carrying out their copolymerization by a known method. Though a volatile general purpose good solvent for the polymer of p-DOX could not be found, it was soluble in chloroform, dichloromethane and the like at the aforementioned ratio, so that it was able to obtain the object complex porous article by the same method of Example 1. Also, since the aforementioned copolymer shows a rubber-like property having higher plasticity than that of the D,L-lactic acid/glycolic acid copolymer P (DLLA-GA) of Example 4, volume ratio of the bioceramics powder when particle size of said powder is 3 μm can be increased to 70% by volume (85% by weight), so that this complex porous article can avoid reactions in the living body caused by the degradation products of the copolymer to the utmost, and activity of the bioactive bioceramics powder is exhibited markedly effectively. Particularly, since its hydrophilic nature is higher than that of PDLLA due to characteristics of p-DOX, it is considered that this complex porous article is effective as a scaffold or the like for the regeneration of cartilage in proliferating cells by ex vivo (in vitro dish).

As has been described in the foregoing, since the implant material of the invention comprising an organic-inorganic complex porous article contains a bioceramics powder in a biodegradable and bioabsorbable polymer in a large amount under uniformly dispersed condition, a humor and the like quickly permeate through the large pore size continuous pores formed inside thereof, so that binding with a living bone and regeneration of a living bone tissue can be effected at an early stage by bone conduction of the bioceramics powder exposed to the porous article surface and the inner face of continuous pores, and it has a practical strength necessary for clinical applications and can be produced easily and accurately by the production method of the invention. Accordingly, as described in the foregoing, this implant material is practically used as a scaffolding for the reconstruction of living bone tissue, a prosthetic material, a bone filler, an inclusion between other implant and a living bone tissue, a substitute for spongy bone, a carrier for sustained drug release and the like.

Next, typical embodiments of the implant material in which the aforementioned organic-inorganic complex porous article of the present invention is applied are described in detail with reference to the drawings. Such an implant material is roughly divided into a type in which the aforementioned porous article is united with other compact biodegradable and bioabsorbable member and another type in which the aforementioned porous article is united with a bio-non-absorbable member, and various embodiments shown in FIG. 1 to FIG. 15 can be exemplified as main cases of the former implant material, and the embodiments shown in FIG. 16 and FIG. 17 as main cases of the latter implant material.

The implant material 10 shown in FIG. 1 is an implant material for fixing median incision closed sternum, as a typical example of the bioactive and biodegradable and bioabsorbable implant material for fixing a bone, which is embedded when a bone of a region where trabecula became rough and thin caused by the reduction of the bone or atrophy of the bone tissue due to osteoporosis is incised or cut or when a defect part of a bone is closed and connected by a surgical operation.

This implant material 10 has an organic-inorganic complex porous article 1 and a pin 2 as a biodegradable and bioabsorbable member, the pin 2 passes through the porous article 1, and both termini of the pin are projected from said porous article 1. In addition, in order to prevent revolution when embedded in a sternum, the pin 2 is formed into a prismatic shape and the porous article 1 is formed into a rectangular prism shape. Also, in order to facilitate insertion into a hole formed in the marrow of the sternum (spongy bone), both termini of the pin 2 are formed into a pyramidal shape, and in order to prevent slipping of the pin 2 from the just described hole, a concavo-convex structure 2a having a saw tooth-like section is formed on the surface of the both termini of this pin 2. In this connection, the pin 2 may be formed into a columnar shape, and the porous article 1 into a cylindrical shape, and the concavo-convex structure 2a of both termini of the pin may be omitted.

The porous article 1 is the same as the aforementioned organic-inorganic complex porous article, namely a biodegradable and bioabsorbable porous article having continuous pores, in which a bioactive bioceramics powder is substantially uniformly dispersed in a biodegradable and bioabsorbable polymer, wherein a part of the bioceramics powder is exposed to the inner face of the pores or the inner face of the pores and the porous article surface. With respect to this porous article 1, porosity, pore size of the continuous pores, ratio of the continuous pores occupying the total pores, the biodegradable and bioabsorbable polymer, the bioceramics powder, percentage content of said powder and the like are as described in the foregoing.

This porous article 1 is prepared in accordance with the aforementioned production method, by forming a porous fiber aggregate molding through compression molding of a nonwoven fabric-like fiber aggregate into a rectangular prism shape under heating, and punching a square hole for pin 2 insertion (a square hole having a size slightly smaller than the pin 2) on the rectangular prism shape organic-inorganic complex porous article obtained by soaking this molding in a volatile solvent.

The dimensions of this porous article 1 can be selected in response to each clinical case, and though the size is not particularly limited, it is necessary to pay attention so that it does not become too large (many). In the case of an implant material for sternum fixing, it is desirable to set length of the porous article 1 to approximately from 10 to 15 mm, and its width to approximately from 6 to 20 mm, and its height to approximately from 6 to 15 mm. It is needless to say that its selection within this range depends on the structure of sternum of each patient. When each dimension of the porous article 1 is smaller than the lower limit of the aforementioned range, bone tissues to be conducted and formed on the porous article 1 becomes less. In this connection, it is needless to say that preferred dimensions of this porous article 1 also change in response to each embedding bone.

Functional effects of this porous article 1 can be increased by containing the aforementioned ossification factors, growth factors, drugs and the like in an appropriate amounts. When an ossification factor or a growth factor is contained, ossification is considerably accelerated in the porous article 1 so that the porous article 1 is substituted with a bone tissue at an early stage and both of the incised and closed half-sternum parts are directly bonded. Also, when it is impregnated with a drug, the drug is directly absorbed into both of the half-sternum parts so that sufficient drug effect is exerted. In addition, it is desirable to effect penetration and proliferation of osteoblast more effectively by improving wettability through the application of the aforementioned oxidation treatment to the surface of this porous article 1.

On the other hand, the aforementioned pin 2 comprises crystalline polylactic acid, polyglycolic acid and the like biodegradable and bioabsorbable polymers whose safety has been confirmed, and particularly, a high strength pin 2 comprising a biodegradable and bioabsorbable polymer having a viscosity average molecular weight of 150,000 or more, preferably approximately from 200,000 to 600,000, is suitably used. Also can be used suitably are a pin comprising a complex body in which approximately from 10 to 60% by weight of the aforementioned bioactive bioceramics powder is mixed with these biodegradable and bioabsorbable polymers, and a pin whose strength is further improved through the orientation of molecules and crystals of the aforementioned polymers by compression molding, forged molding, stretching or the like method. Particularly, those which have a compact quality obtained by orientating polymer molecules and crystals in three dimensional directions by a forged molding are suitably employed.

In the case of an implant material for sternum fixing, it is desirable that length of the pin 2 is approximately from 20 to 40 mm, because less than 20 mm is too short as a pin for sternum fixing, and when longer than 40 mm, on the other hand, it causes an inconvenience in that the pin can hardly be put into the marrow of sternum (spongy bone). Also, it is desirable that width of the pin 2 is approximately from 2 to 4 mm, and it is desirable that its height is approximately from 2 to 3 mm. When width of the pin 2 is narrower than 2 mm and its height is smaller than 2 mm, it becomes so thin that the pin 2 would break, and when width of the pin 2 is broader than 4 mm and its height is larger than 3 mm, on the other hand, it cannot be used because its combination with the porous article 1 exceeds thickness of the sternum. In this connection, the dimensions of the aforementioned pin are desirable dimensions in the case of an implant material for sternum fixing to the utmost, and it is needless to say that desirable dimensions of the pin change in response to the embedding bone.

Figure 2:
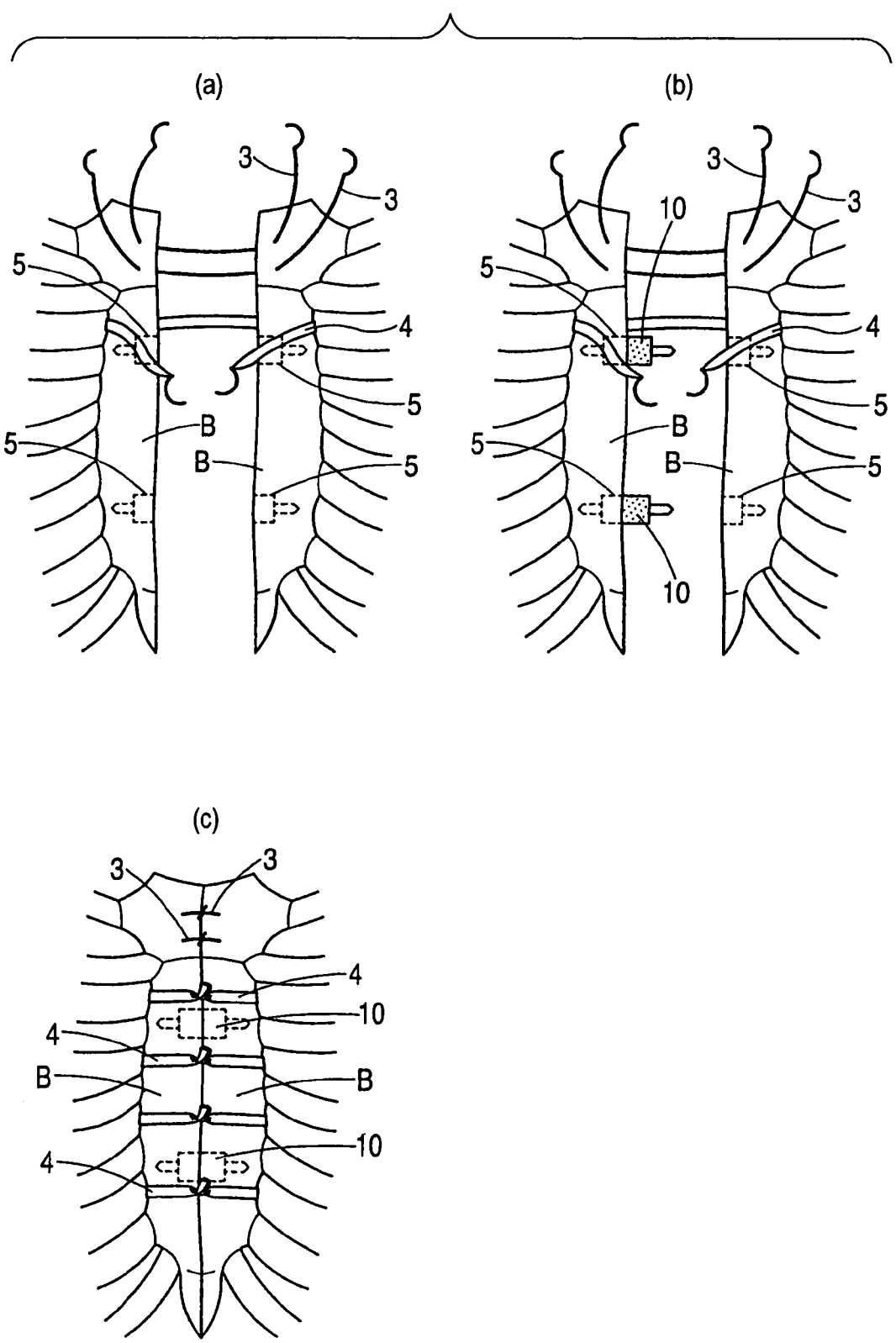
FIGS. 2(a), (b) and (c) are explanatory drawings showing application examples of the implant material of the same embodiment.

Next, using examples of the aforementioned implant material 10 for sternum fixing are described with reference to FIG. 2.

Firstly, as shown in FIG. 2(A), two steel wires 3 and 3 are inserted into median-incised right and left half-sternum parts B and B using a pick, and a binding tape 4 is wrapped around the half-sternum parts B and B through the intercostal space. Though only one tape of this binding tape 4 is wrapped in FIG. 2(A), two or more tapes (generally four) are wrapped by vertically keeping spaces. Then, two or more of hole 5 (a hole having a size slightly smaller than the implant material 10) into which a one side half of the implant material 10 for sternum fixing can be inserted are formed by scraping out with a Kocher clamp or the like unnecessary spongy bones of both of the half-sternum parts B and B.

Next, as shown in FIG. 2(B), one side half of the implant material 10 is inserted into each hole 5 of the one side half-sternum part B by firmly pushing it so that it does not slip out. Then, as shown in FIG. 2(C), both of the half-sternum parts B and B are closed by pulling the steel wires 3 and 3 and thereby pushing the opposite side half of each of the implant material 10 into each hole 5 of the other half-sternum part B, distal parts of the wires 3 and 3 are firmly ligated by adding several knots, and each binding tape 4 is also firmly ligated by adding several knots at the same time. In this connection, though the steel wire 3 and binding tape 4 are used in this embodiment for fixing the half-sternum parts B and B, a band formed from a biodegradable and bioabsorbable polymer such as the aforementioned polylactic acid or from a mixture of this polymer with a bioceramics powder can also be used.

When the implant material 10 for sternum fixing is embedded in the marrow of an incised and closed sternum as described in the above, in the initial stage after embedding, pin 2 of the implant material 10 sticks as a "wedge" into the marrow (spongy bone) of both of the half-sternum parts B and B to exert a reinforcing action by fixing both of the half-sternum parts B and B, so that fixing stability of both of the half-sternum parts is improved. In addition, effected by the bone conduction ability of the bioceramics powder exposing on the surface of the porous article 1 of this implant material 10, a bone tissue is conducted and formed on the surface of the porous article 1, and the porous article 1 and both of the half-sternum parts B and B are bonded within a short period, so that fixing stability and strength of the half-sternum parts B and B are improved by this bonding too.

According to this implant material 10, hydrolysis of the pin 2 and porous article 1 progresses by their contact with humors in the marrow, but the porous article 1 is hydrolyzed more quickly because humors penetrate into its inner part through the continuous pores, and what is more, since a bone tissue is conducted and formed in the inner part by the bone conduction ability of the bioceramics powder exposing to the inner surface of the pores, this porous article 1 is replaced by the bone tissue and disappears within a relatively short period of time. Particularly, when the porous article 1 is impregnated with the aforementioned growth factor, growth of the bone tissue is quick and the porous article 1 is replaced by the bone tissue within a short period. Accordingly, since the closed sternum (half-sternum parts B and B) is directly bonded by the bone tissue substituted with the porous article 1, fixing of the sternum is stabilized by the newly formed bone even in case that the spongy bone of an osteoporosis sternum bone becomes extremely hollow and porous and thereby forms a wafer state and becomes brittle.

On the other hand, hydrolysis of the pin 2 of the implant material 10 gradually progresses by its contact with humors and significantly progresses at the time when the porous article 1 is replaced by a bone tissue, and the porous article becomes fine pieces soon thereafter and finally disappears by completely absorbed by the living body. In that case, when the pin 2 comprises the aforementioned complex body of a biodegradable and bioabsorbable polymer and a bioceramics powder, the pin 2 also shows bone conduction ability, so that a bone is conducted and formed by the repetition of its hydrolysis and replacement of osteoblast and osteoclast by the bioceramics powder, the pin 2 is replaced by the bone tissue accompanied by the phagocytic reaction of degraded fine pieces, and the hole where the pin 2 was stuck into is finally filled with a neoplastic bone and disappears.

The implant material 10 of the invention for bone fixation comprising organic-inorganic complex porous article 1 and pin 2 is not only used by embedding it in a sternum incised and closed by a sternum median incision closing operation as described in the above, but also used by embedding it when a bone of a region where trabecula became rough and thin caused by the reduction of the bone or atrophy of the bone tissue due to osteoporosis is incised or cut or when a defect part of a bone is closed and connected by a surgical operation, and can firmly connect and fix a bone by finally replaced by the bone tissue.

Figure 3:
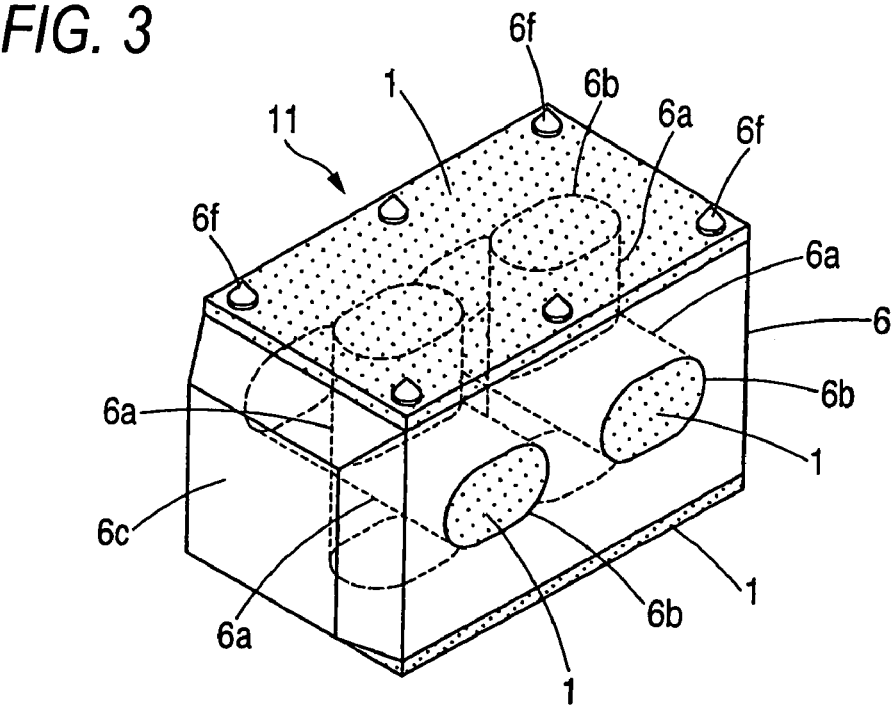
FIG. 3 is a perspective illustration showing another embodiment of the implant material according to the invention.
Figure 6:
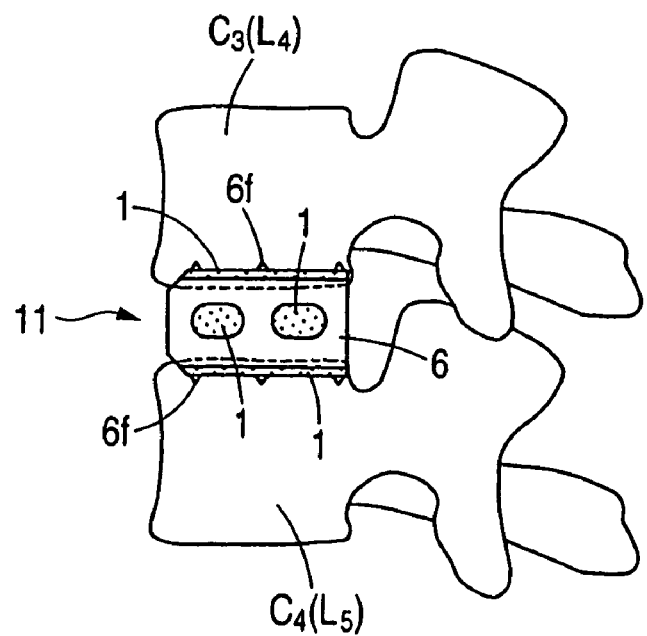
FIG. 6 is an explanatory drawing showing an application example of the implant material of the same embodiment.

As shown in FIG. 6, the implant material 11 shown in FIG. 3 is used as an intervertebral spacer or the like vertebral body fixing material, mainly by inserting between cervical vertebrae $C_3$ and $C_4$ or between lumbar vertebrae $L_4$ and $L_5$. This implant material 11 comprises an organic-inorganic complex porous article 1 and a matrix 6 which is a biodegradable and bioabsorbable member equipped with a cavity 6*a* opening toward the outside, and the porous article 1 is set in the cavity 6*a* of the matrix 6 and partly exposed from an inlet 6*b* of said cavity 6*a*, and the porous article 1 is also arranged on the upper and lower sides of the matrix 6 by superposing in a plate shape. The porous article 1 on the upper and lower sides of the matrix 6 is used as a substitute for an auto-bone and, as will be described later, arranged to facilitate early stage binding (fixation) by getting rid of the gap between the matrix 6 and the cervical vertebrae $C_3$ and $C_4$ or the lumbar vertebrae $L_4$ and $L_5$. In this case, the porous article 1 on the upper and lower sides of the matrix 6 can be omitted.

Figure 4:
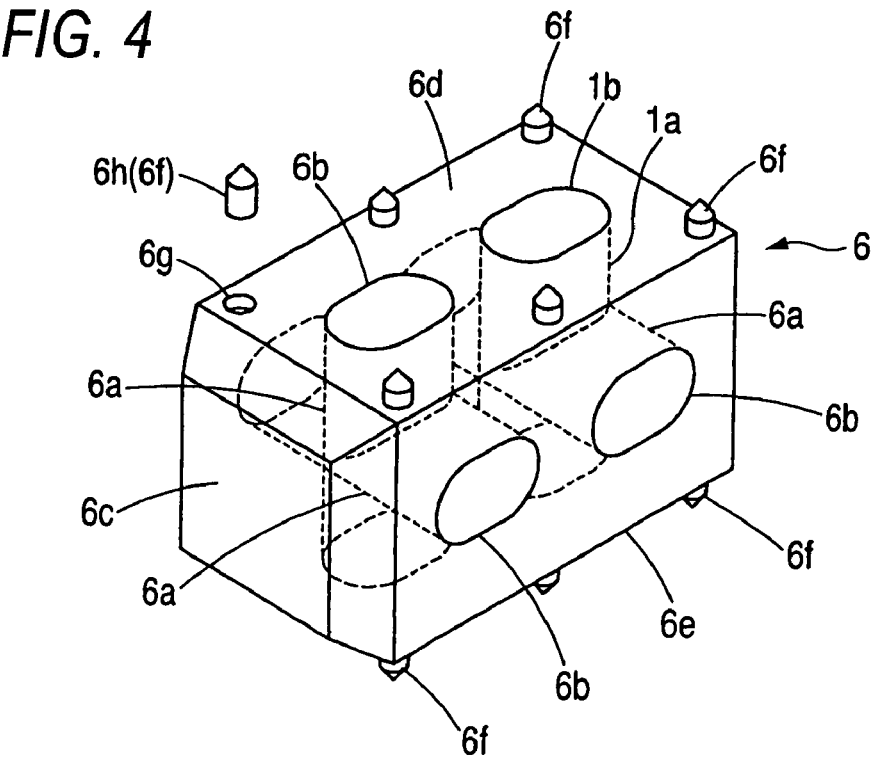
FIG. 4 is a perspective illustration showing a matrix of the implant material of the same embodiment.

The matrix 6 of this implant material 11 is a compact matrix having strength comprising a biodegradable and bioabsorbable polymer containing a bioactive bioceramics powder and, as shown in FIG. 4, formed into a rectangular prism shape. Two lengthwise through perforating cavities 6*a* and two crosswise through perforating cavities 6*a*, opening toward the outside, are formed on this matrix 6 in a mutually crossing manner, and inlets 6*b* of these cavities 6*a* are opened in pairs on all four sides of the matrix 6. The inlets 6*b* of these cavities 6*a* are used as the penetrating inlets for humors and the like, and the porous article 1 set into each of the cavities 6*a* is partly exposed from each inlet 6*b*. In this connection, it is possible to form the inlet 6*b* of cavity 6*a* on the front face and rear face of the matrix 6, too, and in that case, it is desirable to form the rear face inlet into a screw hole shape so that the tip of an insertion jig can be screwed into it.

In order to facilitate insertion of this implant material 11 into the gap between the cervical vertebrae $C_3$ and $C_4$ or between the lumbar vertebrae $L_4$ and $L_5$, four edges of the front face 6c of the matrix 6 are chamfered. Also, in order to make the implant material 11 into an independent type (not requiring an auxiliary fixing material) which does not cause displacement and removal after its insertion into the gap between the cervical vertebrae $C_3$ and $C_4$ or between the lumbar vertebrae $L_4$ and $L_5$, several (6 for each in the drawing) projections 6f for fixation are arranged on both upper and lower faces 6d and 6e of the matrix 6, and the tip part of each projection 6f is stuck out from the porous article 1 of the upper and lower faces of the matrix 6. As shown in FIG. 4, this projection 6f is prepared by forming a concave hole 6g on the upper and lower faces of the matrix 6, and putting a pin 6h (6f) having a pointed conical tip and comprising the same biodegradable and bioabsorbable polymer of the matrix 6 into the concave hole 6g. In this connection, a stabbing piece or the like having a sharp tip may be used instead of the pin 6h, and the projection 6f and the matrix 6 may be formed integrally.

Figure 5:
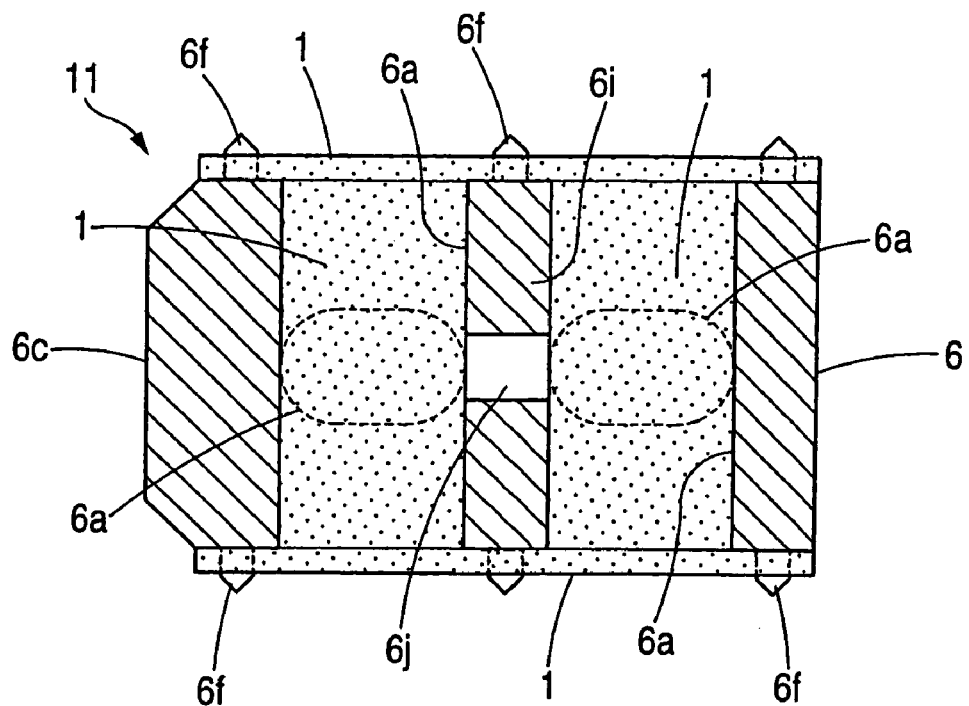
FIG. 5 is a longitudinal sectional view showing the implant material of the same embodiment.

As shown in FIG. 5, a communication hole 6j is formed on a wall part 6i between the two lengthwise cavities 6a and 6a of the matrix 6 so that, as will be described later, a bone tissue to be conducted and formed on the porous articles 1 and 1 set into the cavities can be connected through the communication hole 6j. This wall part 6i is taking a role in increasing compressive strength of the matrix 6.

Regarding the size of matrix 6, its fore and aft dimension is approximately from 18 to 30 mm, and its above and below height dimension and right and left width dimension are approximately from 6 to 24 mm, and when those having various sizes are assorted within these ranges, a matrix fitted to the size of the cervical vertebrae $C_3$ and $C_4$ or the lumbar vertebrae $L_4$ and $L_5$ and to the intervertebral dimension can be selected and inserted.

In the matrix 6 of this implant material 11, the lengthwise and crosswise cavities 6a are formed into a through hole shape having racetrack section, but they may be formed into through hole shapes having square, circular, oval and the like various sections. In addition, it is possible to make the entire inner portion of the matrix 6 into a hollow chamber-like cavity and to effect communication of the cavity with the outside by forming inlet of said cavity on all four faces of the matrix 6.

In this connection, the cavity 6a passing through the matrix 6 in the crosswise direction can be omitted, because when the cavity 6a passing through it in the lengthwise direction is present, a bone tissue is conducted and formed from the upper and lower cervical vertebrae $C_3$ and $C_4$ or lumbar vertebrae $L_4$ and $L_5$ and fused and fixed to the porous article 1 set in its inside. In addition, the inlets 1b on the right and left two sides of the matrix 6 can also be omitted.

The aforementioned matrix 6 comprises a biodegradable and bioabsorbable polymer containing a bioactive bioceramics powder, and the polymers using the pin 2 of the aforementioned implant material 10, namely crystalline poly-L-lactic acid, polyglycolic acid and the like whose safety in the living body has been confirmed are desirably used as the material biodegradable and bioabsorbable polymer, and particularly, a high strength matrix 6 prepared using poly-L-lactic acid having a viscosity average molecular weight of 150,000 or more, preferably approximately from 200,000 to 600,000, is suitable. Such a matrix 6 is produced by a method in which a material biodegradable and bioabsorbable polymer is subjected to injection molding or a molded block of the material biodegradable and bioabsorbable polymer is subjected to cutting work. In the latter method, a matrix 6 obtained by subjecting a molded block to a compression molding, forged molding or the like means to form a block in which the polymer molecules and crystals are oriented and then subjecting this to cutting work is markedly suitable, because it has a compact quality and its strength is further improved due to the three dimensionally oriented polymer molecules and crystals. In addition to this, a block prepared by stretch-molding as a molded block can also be used suitably, and it is also desirable to increase its strength by carrying out a cutting work in such a manner that the stretching direction (orientation direction) becomes lengthwise.

As the bioceramics powder to be contained in this matrix 6, all of the aforementioned bioactive totally absorbable bioceramics powders can be used, and similar to the case of the aforementioned pin 2 of implant material 10, it is desirable to control its percentage content at from 10 to 60% by weight. Formation of bone conduction by the bioceramics powder becomes insufficient when it is less than 10% by weight, and the matrix 6 becomes fragile when it exceeds 60% by weight.

On the other hand, the porous article 1 to be filled in the cavity 6a of the matrix 6 is identical to the aforementioned organic-inorganic complex porous article, namely a biodegradable and bioabsorbable porous article having continuous pores, in which a bioactive bioceramics powder is substantially uniformly dispersed in a biodegradable and bioabsorbable polymer, wherein a part of the bioceramics powder is exposed to the inner face of the pores or the inner face of the pores and the porous article surface. With respect to this porous article 1, porosity, pore size of the continuous pores, ratio of the continuous pores occupying the total pores, the biodegradable and bioabsorbable polymer, the bioceramics powder, percentage content of said powder and the like are as described in the foregoing.

Also, the upper and lower porous articles 1 of the matrix 6 are superposed on the upper and lower surfaces 6d and 6e of the matrix 6 by forming a hole for passing the projection 6f of the matrix 6 and fixed by hot welding or the like means. It is desirable that thickness of the upper and lower porous articles 1 of the matrix 6 is approximately from 0.5 to 3 mm, because when it is thinner than 0.5 mm, it becomes difficult to absorb irregularity on the surface of the cervical vertebrae $C_3$ and $C_4$ or lumbar vertebrae $L_4$ and $L_5$ due to compression deformation so that there is a fear of reducing closely contacted property with the cervical vertebrae $C_3$ and $C_4$ or lumbar vertebrae $L_4$ and $L_5$, and when thicker than 3 mm on the other hand, the period of time required for the degradation and absorption and substitution with a bone tissue becomes long.

It is desirable to contain the aforementioned ossification factors, growth factors, drugs and the like in appropriate amounts in the porous article 1 to be filled in the cavity 6a of the matrix 6 and the porous articles 1 to be united by superposing on the upper and lower sides of the matrix 6, and the wettability may be improved by applying the aforementioned oxidation treatment to the surface of the porous article 1.

As shown in FIG. 6, the aforementioned implant material 11 are inserted in a pair of right and left using an insertion jig between the cervical vertebrae $C_3$ and $C_4$ or between the lumbar vertebrae $L_4$ and $L_5$, thereby effecting correction of the distance and posture of the cervical vertebrae $C_3$ and $C_4$ or lumbar vertebrae $L_4$ and $L_5$. When the implant material 11 is inserted in this manner, the upper side and lower side porous articles 1 and 1 of the matrix 6 are compressed by the sandwiching pressure of the cervical vertebrae $C_3$ and $C_4$ or lumbar vertebrae $L_4$ and $L_5$ and closely contacted to the cervical vertebrae $C_3$ and $C_4$ or lumbar vertebrae $L_4$ and $L_5$ without a gap, and the projections 6f on the upper and lower sides of the matrix 6 cut into the spongy bones of the cervical vertebrae $C_3$ and $C_4$ or lumbar vertebrae $L_4$ and $L_5$ at the same time, so that the implant material 11 is fixed without causing displacement and removal and stably arranged due to the rectangular prism shape of the matrix 6.

When the implant material 11 is installed by inserting it between the cervical vertebrae $C_3$ and $C_4$ or lumbar vertebrae $L_4$ and $L_5$ in this manner, hydrolysis of the matrix 6 which has sufficient strength and takes the same role of the cortical bone in the living body gradually progresses from its surface by contacting with the humor. Also, hydrolysis of the porous article 1 which takes the same role of spongy bone quickly progresses from its exposed part by the humor permeating into its inner moiety through the continuous pores, and osteoblast penetrates into the inner moiety of the porous article 1 to conduct and form a bone tissue by the bone conduction ability of the bioceramics powder, so that the porous article 1 is replaced by the bone tissue within a relatively short period of time. Accordingly, the upper, and lower cervical vertebrae $C_3$ and $C_4$ or lumbar vertebrae $L_4$ and $L_5$ are fused and fixed by this substituted bone tissue. On the other hand, the matrix 6 shows a high compressive strength from the early stage similar to the case of a conventional carbon cage and keeps the strength even after bone substitution of the porous article 1, so that it takes a great role in dynamically fixing the implant material 11 through its complete fusion with the cervical vertebrae $C_3$ and $C_4$ or lumbar vertebrae $L_4$ and $L_5$, and its complete replacement by the bone tissue is completed several years (about 5 years) thereafter. At this point of time, complete solid fusion by living bone has been obtained.

Since the upper side and lower side porous articles 1 of the matrix 6 are compressed and thereby closely contacted to the cervical vertebrae $C_3$ and $C_4$ or lumbar vertebrae $L_4$ and $L_5$ without a gap, and similar to the case of the aforementioned organic-inorganic complex porous article, the porous article 1 contains from 60 to 90% by weight of a bioceramics powder having bone conduction ability, has a porosity of from 50 to 90% wherein the continuous pores occupies from 50 to 90% of the total pores and has a pore size of the continuous pores of from roughly 100 to roughly 400 μm, osteoblast can easily penetrate therein so that conduction formation of a bone tissue is carried out accurately, and the implant material 11 is fixed by directly bonding to the upper and lower cervical vertebrae $C_3$ and $C_4$ or lumbar vertebrae $L_4$ and $L_5$ at an early stage when the bone tissue is conducted and formed on the surface layer of both of the upper and lower sides of the porous article 1 of the matrix 6.

Since both of the matrix 6 and porous article 1 are degraded and absorbed and replaced by a bone tissue and do not remain in the living body as foreign matter, this implant material 11 can wipe out a danger of exhibiting harmful effects due to its presence in the living body for a prolonged period of time, as is possible in the titanium or carbon cages conventionally used as vertebral body fixing materials, and a problem of causing its sedimentation into the vertebral body due to incompatibility of dynamical characteristics with the living body. What is more, since the porous article 1 can be replaced by a bone tissue by carrying out a histological action similar to a living bone, it is not necessary to extract an ilium or the like as a transplantation auto-bone for filling in a cage like the conventional case, and a problem of being insufficient in the amount of available auto-bones for transplantation and a problem of complicated treatment at the time of surgical operation after the extraction can also be wiped out.

Though both of the upper and lower faces 6d and 6e of the matrix 6 are horizontal faces in this implant material 11, the matrix 6 may be changed into a tapering shape by slanting front side of the upper face 6d downward and slanting front side of the lower face 6e upward, and an implant material suited for correcting lumber vertebrae to a lordosis position can be obtained by such a changing.

Figure 7:
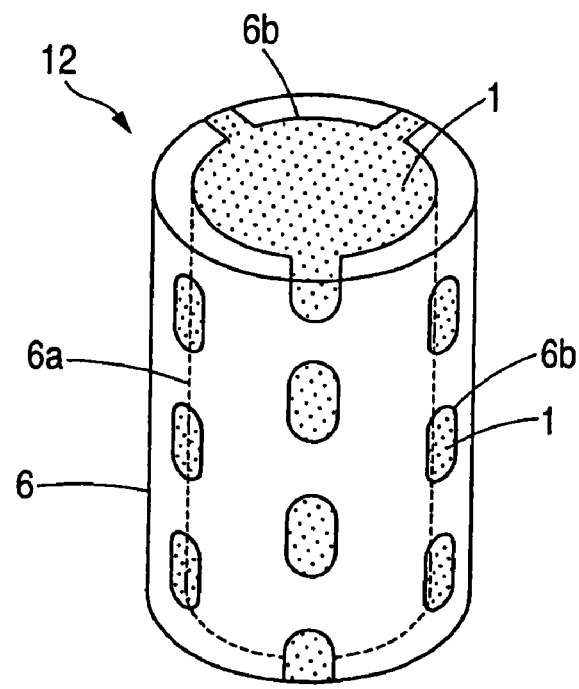
FIG. 7 is a perspective illustration showing still another embodiment of the implant material according to the invention.

Also, shape of the matrix 6 is not limited to the aforementioned rectangular prism shape, and it can be made into various shapes suited for cervical vertebrae, lumber vertebrae, spinal column and the like regions to be used. The implant material 12 shown in FIG. 7 is a result of changing shape of the matrix in such a manner, in which the matrix 6 is formed into a cylindrical shape having a cavity 6a (a cavity whose section is circular) inside thereof, and an inlet 6b of a large circular cavity is formed on each of both terminal faces and an inlet 6b of a small ellipse cavity is formed on its peripheral side in a large number arrange in a staggered manner. In addition, the aforementioned organic-inorganic complex porous article 1 is filled in the cavity 6a of this matrix 6, and the porous article 1 is partly exposed from each of the inlets 6b formed on both terminal faces and peripheral side of the matrix 6.

Such an implant material 12 is inserted between cervical vertebrae, lumber vertebrae and the like vertebral bodies in a vertical direction as shown in the drawing, and similar to the case of the aforementioned implant material 11, the matrix 6 and the porous article 1 are finally replaced by a bone tissue to fuse and fix the upper and lower vertebral bodies.

In this connection, as occasion demands, this implant material 12 may be arranged in sideways by forming a male screw on its peripheral side and screwing it between the upper and lower vertebral bodies.

Figure 8:
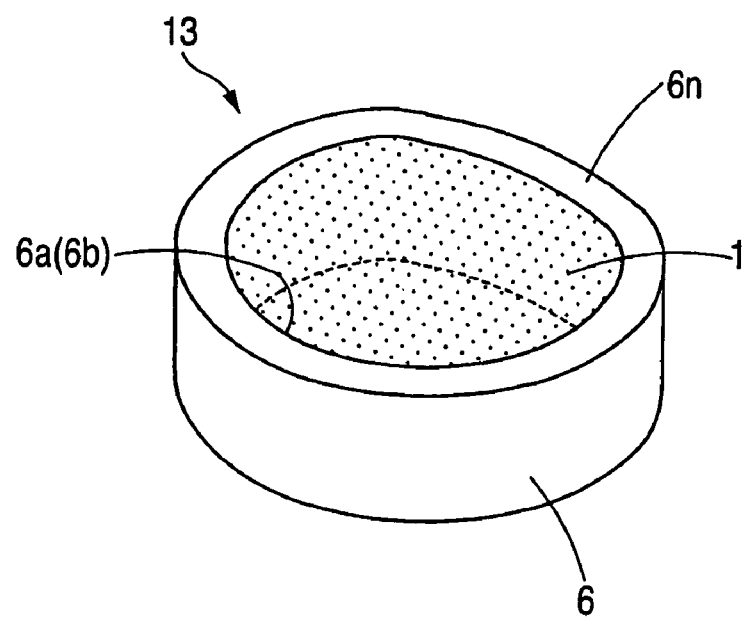
FIG. 8 is a perspective illustration showing still another embodiment of the implant material according to the invention.

The implant material 13 shown in FIG. 8 is also a result of changing shape of the matrix, in which the matrix 6 is formed into a low stature annular shape having a small curvature part 6n, the aforementioned porous article 1 is filled in its inside cavity 6a, and both of the upper and lower sides of the porous article 1 are exposed from the upper and lower inlets 6b of said cavity. Though inlet of the cavity is not formed on the peripheral face of this annular shape matrix 6, two or more inlets of the cavity may be formed as occasion demands. In addition, the aforementioned projections for fixing use may be formed on both of the upper and lower faces of this annular shape matrix 6.

Such an implant material 13 is inserted between cervical vertebrae, lumber vertebrae and the like vertebral bodies with the small curvature part 6n of the matrix 6 being positioned backside, and similar to the case of the aforementioned implant materials 11 and 12, the matrix 6 and the porous article 1 are finally replaced by a bone tissue to fuse and fix the upper and lower vertebral bodies.

Each of the aforementioned implant materials 11, 12 and 13 is inserted and arranged as a vertebral body fixing material between cervical vertebrae, lumber vertebrae and the like vertebral bodies, and it can be used in a bone joint of each region when shape of the matrix 6 is optionally changed.

Figure 9:
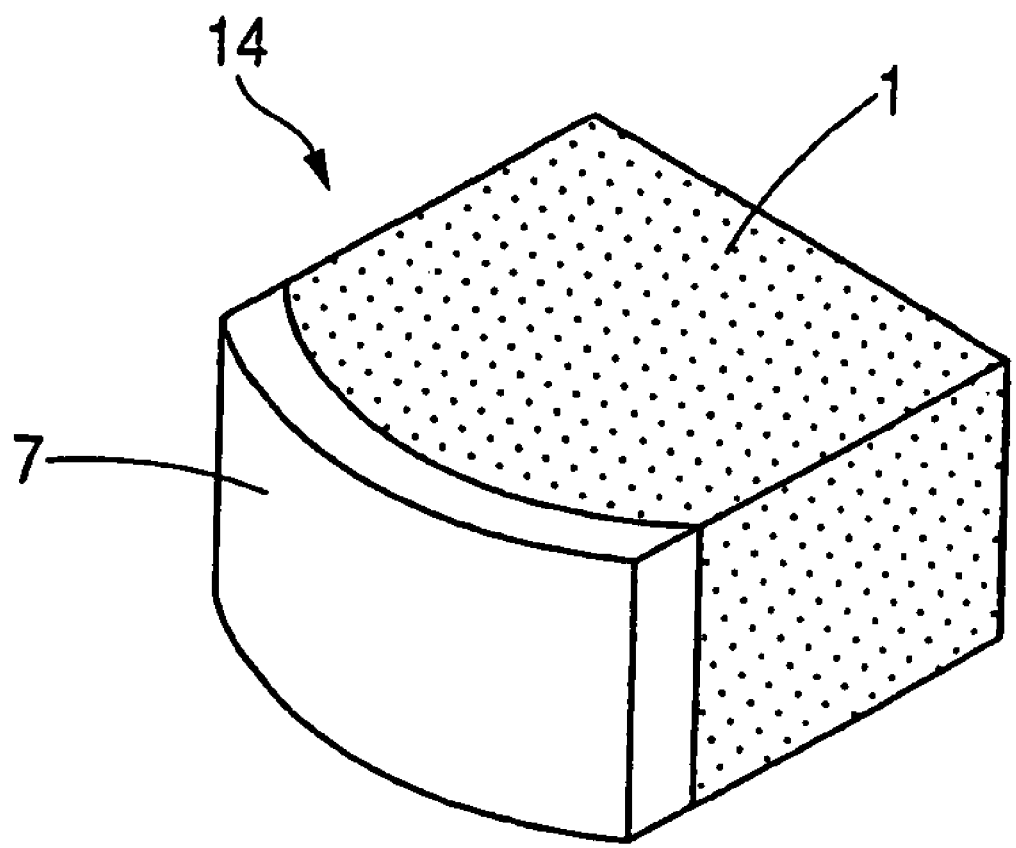
FIG. 9 is a perspective illustration showing still another embodiment of the implant material according to the invention.

The implant material 14 shown in FIG. 9 is embedded in a defect part of a bone as a substitute for a bone allograft or bone autograft (autogenous graft), it has a block shape organic-inorganic complex porous article 1 and a skin layer 7 which is a biodegradable and bioabsorbable member, and this skin layer 7 is superposed on a part of the surface of the porous article 1 and united.

The block shape porous article 1 is identical to the aforementioned organic-inorganic complex porous article, namely a biodegradable and bioabsorbable porous article having continuous pores, in which a bioactive bioceramics powder is substantially uniformly dispersed in a biodegradable and bioabsorbable polymer, wherein a part of the bioceramics powder is exposed to the inner face of the pores or the inner face of the pores and the porous article surface. This porous article 1 is prepared by the aforementioned production method of the invention, and its porosity, pore size of the continuous pores, ratio of the continuous pores occupying the total pores, the biodegradable and bioabsorbable polymer, the bioceramics powder, percentage content of said powder and the like are as described in the foregoing.

This porous article 1 takes a role of a spongy bone, its shape is not particularly limited with the proviso that it has a block shape, and it can be prepared into various shapes in response to the defect part of bone to be treated. This porous article 1 may contain the aforementioned ossification factors, growth factors, drugs and the like in appropriate amounts, and the wettability may be improved by applying the aforementioned oxidation treatment to the surface of the porous article 1 and the surface of the skin layer 7.

The skin layer 7 takes a role of a cortical bone and is a compact and strong layer comprising a biodegradable and bioabsorbable polymer containing a bioactive bioceramics powder. According to this implant material 14, the skin layer 7 is superposed on the convex-curved side face of the block shape porous article 1 and integrated into one body, but it may be arranged by superposing on any one of the other side face, the upper face or the bottom face, or it may be arranged by superposing on two or three or more faces of the porous article 1. In short, this skin layer 7 may be arranged by partly superposing on the faces of the block shape porous article 1.

Though thickness of the skin layer 7 is not particularly limited, it is desirable to optionally set it within the range of from 1.0 to 5.0 mm, by taking into consideration the defect bone part where the implant material 14 is to be embedded. There is a possibility of causing insufficient strength of the skin layer 7 when it is thinner than 1.0 mm, and when thicker than 5.0 mm, it shows disadvantage that a prolonged period of time is required for the degradation and absorption of the skin layer 7 and its subsequent substitution with a bone tissue.

Since this skin layer 7 requires a strength larger than that of the porous article 1, crystalline poly-L-lactic acid, polyglycolic acid and the like are desirably used as the material biodegradable and bioabsorbable polymer, and particularly, a high strength skin layer 7 prepared using poly-L-lactic acid having a viscosity average molecular weight of 150,000 or more, preferably approximately from 200,000 to 600,000, is suitable.

As the bioceramics powder to be contained in this skin layer 7, all of the aforementioned bioactive bioceramics powders to be contained in the porous article 1 can be used, and it is desirable to control its percentage content within the range of from 10 to 60% by weight. The skin layer 7 becomes fragile when it exceeds 60% by weight, and formation of bone conduction by the bioceramics powder becomes insufficient when it is less than 10% by weight.

This skin layer 7 is produced by a method in which a biodegradable and bioabsorbable polymer containing a bioceramics powder is subjected to injection molding or a molded block of the biodegradable and bioabsorbable polymer containing a bioceramics is subjected to cutting work. In the latter method, a skin layer 7 obtained by making a molded block into a block in which the polymer molecules and crystals are oriented by a compression molding, forged molding or the like means and then subjecting this to cutting work is markedly suitable, because it has a compact quality and its strength is further improved due to the three dimensionally oriented polymer molecules and crystals. In addition to this, a skin layer prepared by subjecting a stretch-molded molded block to a cutting work can also be used.

This implant material 14 is obtained by superposing the skin layer 7 prepared by the above method on one convex-curved side face of the block shape porous article 1 and uniting them in an un-separating form by hot welding or the like means. The means for integrating the skin layer 7 and the porous article 1 into one body is not limited to the hot welding, and they may be integrated by other means.

When the implant material 14 having the aforementioned construction is embedded in a defect part of a bone as a substitute for a bone allograft or bone autograft (autogenous graft), and the spongy bone moiety of the defect bone part is filled with the block shape porous article 1, simultaneously filling the cortical bone moiety of the defect bone part with the skin layer 7, the block shape porous article 1 takes a role of the spongy bone and the skin layer 7 having larger strength takes a role of the cortical bone, thus effecting as if the spongy bone moiety of the defect bone part is filled with the spongy bone and the cortical bone moiety is filled with the cortical bone.

When a defect part of a bone is filled with the implant material 14 in this manner, hydrolysis of the block shape porous article 1 quickly progresses because humors penetrate into its inner part through the continuous pores, and osteoblast penetrate into the inner part of the porous article 1 to effect conduction formation of a bone tissue by the bone conduction ability of the bioceramics powder. Because of this, the block shape porous article 1 is replaced by the bone tissue within a relatively short period of time. On the other hand, hydrolysis of the skin layer 7 gradually progresses from the surface falling behind the block shape porous article 1, and the skin layer 7 keeps sufficient strength during a period until the block shape porous article 1 is replaced by a bone tissue in some degree and finally disappears by absorbed by the bone tissue. Since this implant material 14 does not show specific living body reaction as described in the foregoing, it can become an auto-bone by the penetration and substitution of peripheral living bones during its nonspecific degradation, absorption and discharge. That is, since both of the block shape porous article 1 and skin layer 7 are replaced by a bone tissue by their degradation and absorption and do not remain in the living body as foreign matter, a danger of exhibiting harmful effects after a prolonged period of time of existence in the living body, as is possible in conventional implant materials made of ceramics, can be wiped out, and a defect part of bone can be repaired and reconstructed by the replaced bone tissue itself.

Also, since both of the porous article 1 and skin layer 7 of this implant material 14 use a biodegradable and bioabsorbable polymer as the material, unlike the case of the conventional bone allograft which uses a cadaveric bone as the material, there is no need to worry about a shortage of the material so that it is possible to carry out mass production of necessary and sufficient amount of the implant material without limitation, and the material can be made into desired shapes and sizes by molding, cutting work and the like.

In addition, the skin layer 7 of this implant material 14 contains a bioceramics powder, but being comprised of a biodegradable and bioabsorbable polymer, it does not have a disadvantage of being too hard and brittle unlike the case of a baked ceramics implant material, is not easily broken due to its toughness and can be heat-deformed when necessary. Also, the block shape porous article 1 also contains a bioceramics powder in a large amount, but being a porous article which uses a biodegradable and bioabsorbable polymer as the material, even when its porosity is high, it does not show the disadvantage common in the high magnification porous ceramics, namely tattering fallout of fragments even at the time of embedding due to considerable brittleness, and it can be heat-deformed when necessary. Thus, the implant material 14 of the invention does not have brittleness, has sufficient practical strength, is possible to be heat-deformed and has excellent handling ability.

In this connection, this implant material 14 can be used in many applications as a surgical substituent and is particularly effective as prostheses and spacers of cervical vertebrae, lumber vertebrae and the like vertebral bodies, which are now frequently used but having several problems so far revealed.

Figure 10:
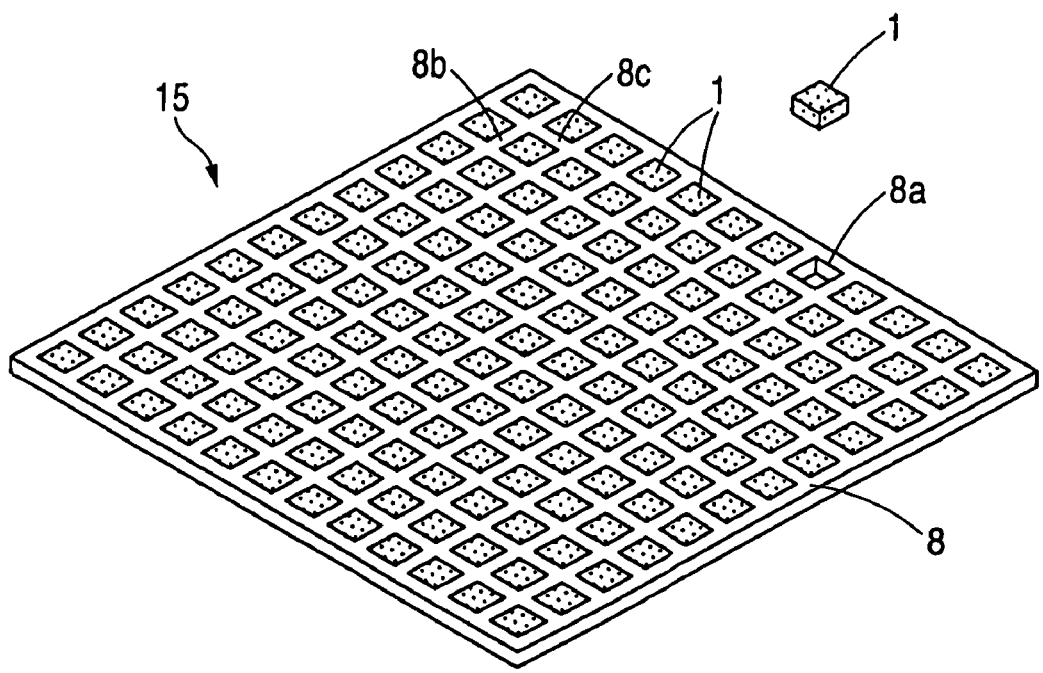
FIG. 10 is a perspective illustration showing still another embodiment of the implant material according to the invention.
Figure 11:
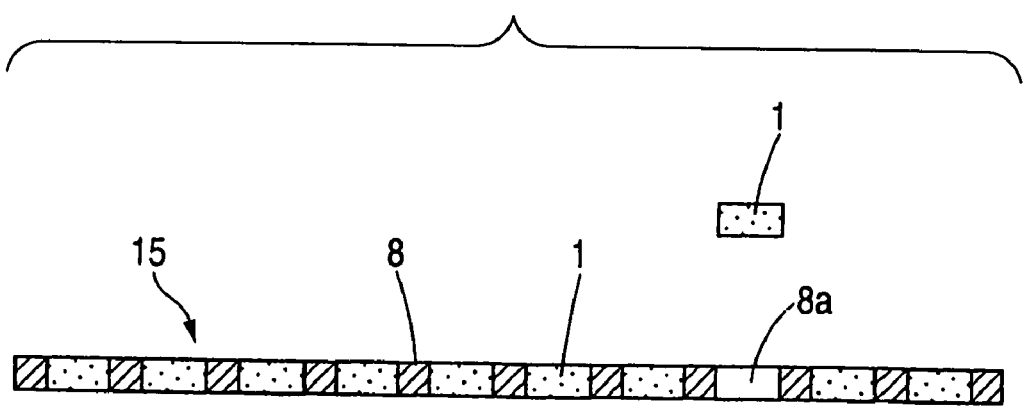
FIG. 11 is a sectional view showing the implant material of the same embodiment.

The implant material 15 shown in FIG. 10 and FIG. 11 is an implant material which is used as prosthetic materials, fillers and the like for the purpose of recovering, correcting or increasing defect or deformed parts of various skeletal regions such as a skull, a jaw, the face, the chest and the like, and it has an organic-inorganic complex porous article 1 and a net-shaped body 8 as a biodegradable and bioabsorbable member, wherein the porous article 1 is filled in a mesh 8a of this net-shaped body 8 and united therewith.

The net-shaped body 8 of this implant material 15 is a compact and strong net-shaped body comprising a biodegradable and bioabsorbable polymer containing a bioactive bioceramics powder, which is obtained by forming the square mesh 8a on a sheet or plate of a biodegradable and bioabsorbable polymer containing a bioactive bioceramics powder by punching, cutting work or the like means. Shape of the mesh 8a is not limited to a square, and it can be made into circular, lozenge and the like desired mesh shapes.

It is desirable that opening area of the mesh 8a is approximately from 0.1 to 1.0 cm$^2$, and it is desirable that area ratio of the mesh 8a occupying the net-shaped body 8 is approximately from 10 to 80%. Also, it is desirable that thickness of the net-shaped body 8 is approximately from 0.3 to 1.5 mm, and it is desirable that width of the warp-corresponding part 8b and weft-corresponding part 8c of the net-shaped body 8 is approximately from 2 to 10 mm. When area ratio of the mesh 8a is less than 10%, general strength of the implant material 15 is large, but filling amount of the porous article 1 having high hydrolyzing rate to be filled in the mesh 8a becomes small and occupying ratio of the net-shaped body 8 having low hydrolyzing rate becomes large, thus resulting in a prolonged period of time required for the complete degradation and absorption of the implant material 15 and subsequent replacement by a bone tissue. On the other hand, when area ratio of the mesh 8a exceeds 80%, thickness of the net-shaped body 8 becomes thinner than 0.3 mm and width of the warp-corresponding part 8b and weft-corresponding part 8c becomes narrower than 2 mm, strength of the net-shaped body 8 is considerably reduced so that it becomes difficult to obtain an implant material 15 having large strength.

Figure 12:
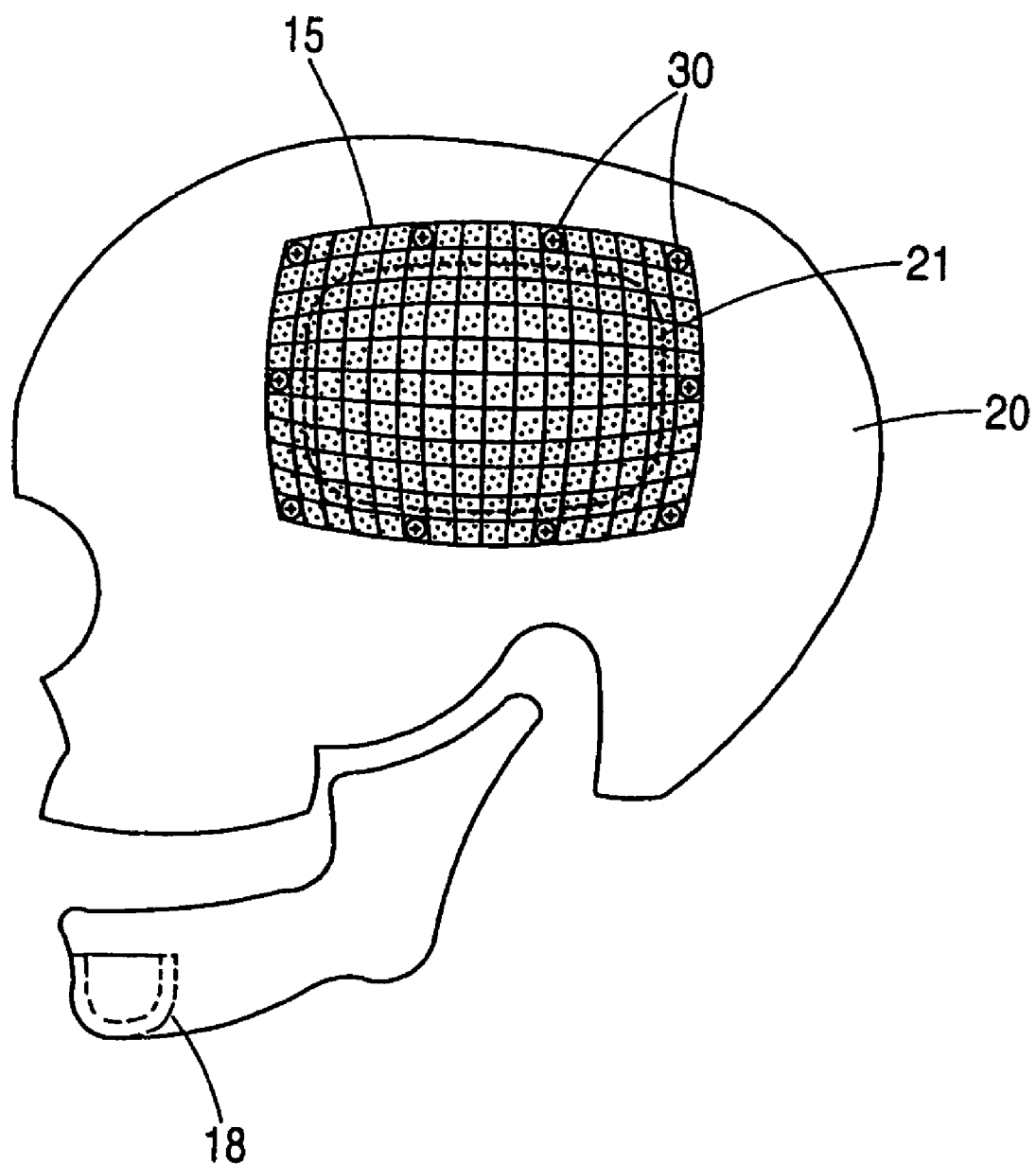
FIG. 12 is an explanatory drawing showing an application example of the implant material of the same embodiment.

When a net-shaped body 8 having good bending workability is wanted, a melt-molded product of a biodegradable and bioabsorbable polymer containing a bioceramics powder is once forged at a cold condition (a temperature range of from glass transition temperature of the polymer to its melting temperature) and again forged at a cold condition by changing the direction (mechanical direction MD), and using this as the aforementioned sheet or plate to be used as the material, a net-shaped body is prepared by forming the mesh 8a thereon by punching, cutting work or the like means. According to the biodegradable and bioabsorbable polymer sheet or plate forged twice by changing directions in this manner, the molecular chain, molecular chain aggregation domain, crystals and the like of the biodegradable and bioabsorbable polymer are multi-axially oriented or an aggregated structure of a large number of multi-axially oriented clusters is formed, so that when this is subjected to bending deformation at an ordinary temperature range (0 to 50° C.), the shape is maintained and hardly returned to the original shape at around the body temperature (30 to 40° C.), and whitening and breakage hardly occur when the bending deformation is carried out many times. Accordingly, since the implant material 15 prepared using the net-shaped body 8 obtained by forming the mesh 8a on this sheet or plate has good bending workability, it is possible, for example as shown in FIG. 12, to fix the implant material 15 to a defect part 21 of a skull 20 by bending it into a shape identical to the curved face of said defect part 21, at ordinary temperature during an operation. In this connection, as a sheet or plate to be used as the material of the net-shaped body 8, those which are monoaxially or biaxially oriented, not oriented or compression molded may be used as a matter of course.

As the material biodegradable and bioabsorbable polymer of the net-shaped body 8, crystalline poly-L-lactic acid, poly-D-lactic acid, poly-D/L-lactic acid, polyglycolic acid and the like whose safety in the living body has been confirmed are desirably used. When the strength, hydrolyzing rate and the like of the net-shaped body 8 are taken into consideration, such biodegradable and bioabsorbable polymers having a viscosity average molecular weight of 150,000 or more, preferably approximately from 200,000 to 600,000, are used.

As the bioceramics powder to be contained in the biodegradable and bioabsorbable polymer of this net-shaped body 8, all of the aforementioned bioactive bioceramics powders to be contained in the porous article 1 can be used, and it is desirable to control its percentage content within the range of from 10 to 60% by weight. Formation of bone conduction by the bioceramics powder becomes insufficient when it is less than 10% by weight and the net-shaped body 8 becomes fragile when it exceeds 60% by weight.

In this connection, a net-shaped body prepared for example by fusing warp and weft of a biodegradable and bioabsorbable polymer containing a bioceramics powder (flat-sectioned ones are included as the yarn, in addition to circular-sectioned ones) at their crossing points may be used instead of the aforementioned net-shaped body 8.

On the other hand, the porous article 1 to be filled in each mesh 8a of the aforementioned net-shaped body 8 is the same as the aforementioned organic-inorganic complex porous article, namely a biodegradable and bioabsorbable porous article having continuous pores, in which a bioactive bioceramics powder is substantially uniformly dispersed in a biodegradable and bioabsorbable polymer, wherein a part of the bioceramics powder is exposed to the inner face of the pores or the inner face of the pores and the porous article surface. Porosity of this porous article 1, pore size of the continuous pores, ratio of the continuous pores occupying the total pores, the biodegradable and bioabsorbable polymer, the bioceramics powder, percentage content of said powder and the like are as described in the foregoing.

The aforementioned ossification factors, growth factors, drugs and the like may be contained in this porous article 1 in appropriate amounts, and the wettability may be improved by applying the aforementioned oxidation treatment to the surface of the porous article 1 and net-shaped body 8.

As shown in FIG. 12, for example, the implant material 15 having the aforementioned construction is put on the skull 20 covering the defect part 21 of the skull 20, and several positions of its fringing region are fixed with a screw 30 comprising a biodegradable and bioabsorbable polymer. In that case, the implant material 15 is preferably subjected to bending to match it with the curved face of the defect part 21 of the skull 20.

When the defect part 21 of the skull 20 is covered with the implant material 15 in this manner, hydrolysis of the net-shaped body 8 gradually progresses from the surface through its contact with humors, and hydrolysis of the porous article 1 quickly progresses due to penetration of humors into its inner part through the continuous pores. Also, osteoblast penetrate into the inner part of the porous article 1 to effect conduction formation of a bone tissue by the bone conduction ability of the bioceramics powder contained in the porous article 1, so that the porous article 1 is replaced by the bone tissue within a relatively short period of time. On the other hand, hydrolysis of the net-shaped body 8 progresses falling behind the porous article 1, and the net-shaped body 8 keeps sufficient strength during a period until the porous article 1 is replaced by a bone tissue in some degree so that protect the defect part 21 of the skull 20. Thereafter, the net-shaped body 8 also disappears finally by replaced by the bone tissue.

Since both of the porous article 1 and the net-shaped body 8 of this implant material 15 are replaced by a bone tissue by their degradation and absorption and do not remain in the living body as foreign matter, a danger of exhibiting harmful effect after a prolonged period of time of existence in the living body, as is possible in metal punching plates conventionally used as prosthetic materials of defect parts of bones, can be wiped out, and the defect part 21 of the skull 20 can be repaired and reconstructed by the replaced bone tissue.

In addition, the net-shaped body 8 of this implant material 15 contains a bioceramics powder, but being comprised of a biodegradable and bioabsorbable polymer, it does not have a disadvantage of being too hard and brittle unlike the case of baked compact ceramics, is not easily defect due to its toughness and can be heat-deformed at ordinary temperature. In addition, the porous article 1 also contains a bioceramics powder in a large amount, but since it uses a biodegradable and bioabsorbable polymer as the matrix, even when its porosity is high, it does not show the problem common in high magnification porous ceramics which cause tattering fallout of fragments even during their filling due to considerable brittleness, and it can be heat-deformed when necessary. Thus, the implant material 15 does not have brittleness, has sufficient practical strength, is possible to be heat-deformed and has excellent handling ability.

It was able to make this implant material 15 as a living bone substitute of a high area and less material by making a net-shaped body taking a role of high strength cortical bone and by increasing porosity of the porous article which takes a role of a spongy bone, and being a combination of the net-shaped body and porous article, the total amount of their materials was restricted to a level as small as possible, so that this is an implant material containing small contents to be treated by the living body during its degradation absorption process and having excellent biocompatibility.

In this connection, in addition to the application example shown in FIG. 12, this implant material 15 is used for the restoration and reconstruction of relatively large defect parts of bones, such as filling of depressed fracture of central face and filling of parts after extraction of foci of bone tumor and the like, and is also used as a base material for bone extension.

Figure 13:
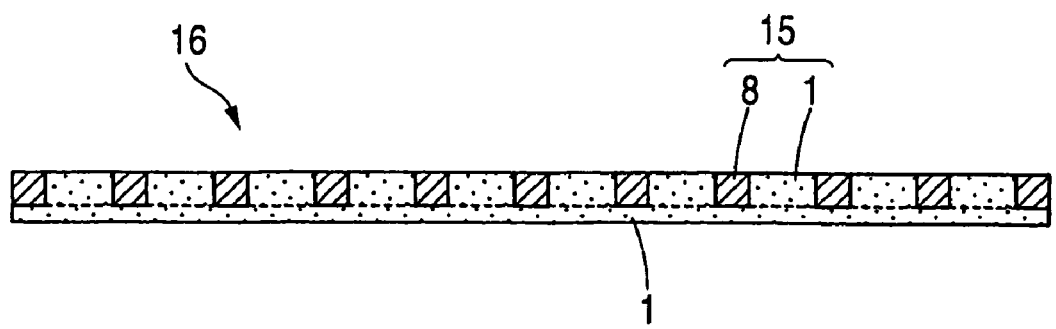
FIG. 13 is a sectional view showing still another embodiment of the implant material according to the invention.
Figure 14:
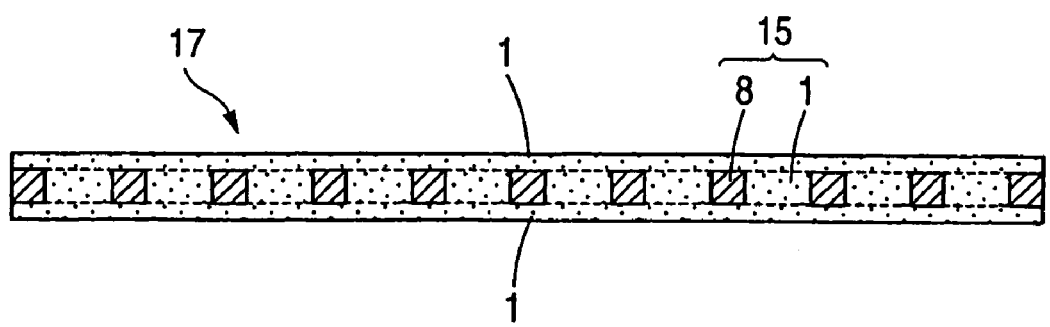
FIG. 14 is a sectional view showing still another embodiment of the implant material according to the invention.

According to the aforementioned implant material 15 which is a combined type of the porous article 1 and the net-shaped body 8, not only filling of the porous article 1 into the mesh 8a of net-shaped body 8, but also construction of a structure by further arranging the porous article 1 in layers on one side or both sides of the net-shaped body 8 is a leading embodiment. FIG. 13 and FIG. 14 show implant materials 16 and 17 of such an embodiment, in which in the case of the implant material 16, the aforementioned organic-inorganic complex porous article 1 is arranged in a layer shape on one side of the aforementioned implant material 15, and in the case of the implant material 17, the aforementioned organic-inorganic complex porous article 1 is arranged in a layer shape on both sides of the aforementioned implant material 15.

The layer shape porous article 1 is identical to the aforementioned organic-inorganic complex porous article 1, which is prepared in a layer form (sheet form) by the aforementioned production method of the invention. This layer shape porous article 1 is integrally laminated on one side or both sides of the implant material 15 by heat fusion or the like means. Thickness of this layer shape porous article 1 is not particularly limited, but when its close adhesion to peripheral bone of a defect bone part and a period required for its degradation and absorption and subsequent substitution with a bone tissue are taken into consideration, it is desirable to set it to a thickness of approximately from 0.5 to 3 mm.

Since a bone tissue is formed on one side or both sides of such implant materials 16 and 17 almost uniformly during a relatively short period of time, facial restoration and reconstruction of the defect bone part are quickly carried out. Also, since the porous article 1 arranged in a layer form is closely contacted to the peripheral bone of the defect bone part by taking a role as a cushion material, and osteoblast easily penetrates into the layer form porous article 1, a bone tissue is conducted and formed on the surface layer region of the porous article 1 in an early stage, and the implant material 16 or 17 is directly bonded to the peripheral bone of the defect bone part and strongly fixed.

Figure 15:
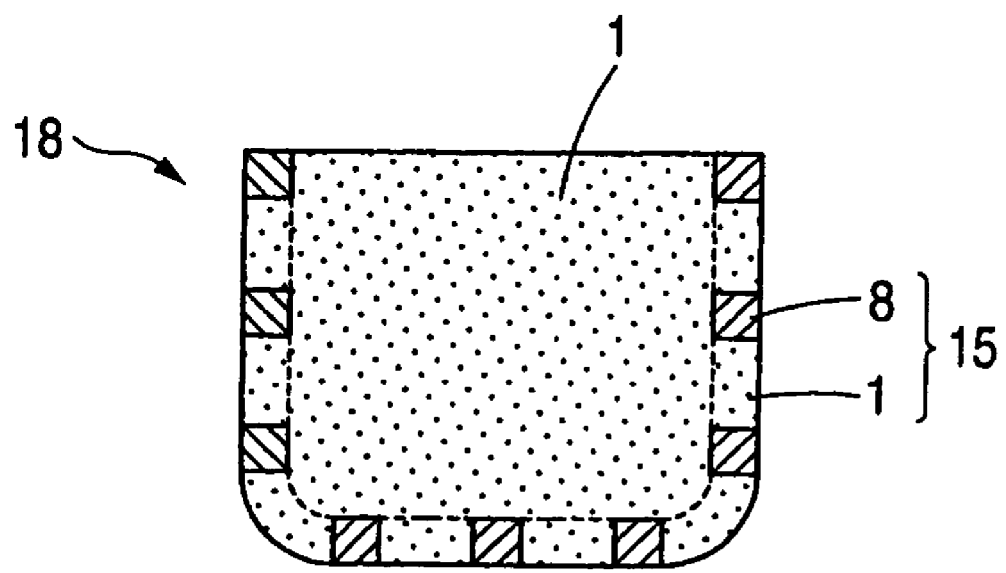
FIG. 15 is a sectional view showing still another embodiment of the implant material according to the invention.

In addition, according to the aforementioned implant material 15 which is a combined type of the porous article 1 and the net-shaped body 8, construction of a structure by concave-curving or convex-curving the net-shaped body 8 and further arranging the porous article 1 inside thereof is also a leading embodiment. FIG. 15 shows an implant material 18 of such an embodiment, and in this implant material 18, the net-shape body 8 of the aforementioned implant material 15 is concave-curved into U-shape, and a porous article 1 identical to the porous article 1 filled in its mesh is also filled in inside of the net-shaped body 8, namely inside of the concave curve. As the net-shaped body 8, a net-shaped body prepared by forming meshes on the aforementioned biodegradable and bioabsorbable polymer sheet or plate, forged twice by changing its mechanical direction to provide good bending workability, is particularly preferably used because of its high mechanical strength and its possibility to carry out bending at ordinary temperature.

Such an implant material 18 is prepared into such a size that it can be embedded and filled into defect parts of, for example, jaw bone and the like, and used for the restoration and reconstruction of a defect part of jaw bone as shown in FIG. 12 by an imaginary line. In addition, with the aim of filling and regenerating a living bone lost by an accident or a cancer, this can also be used suitably for the restoration and reconstruction of not only defect parts of a skull, a central face and an upper jaw, a lower jaw or the like jaw face, but also defect parts of other large bones in the field of orthopedic surgery.

In this connection, though the net-shaped body 8 of the aforementioned implant material 18 is concave-curved into U-shape, the implant material 18 may be prepared by concave-curving or convex-curving the net-shaped body 8 into a shape which corresponds and matches to a defect bone part to be reconstructed, and filling the porous article 1 in its inside, and as occasion demands, the porous article 1 may be further arranged in a layer form on the outside of the implant material 18. In addition, it may be made into an implant material having a structure in which the net-shaped body 8 is folded up and the porous article 1 is also filled between the folded net-shaped body 8, or it may be made into an implant material having a sandwich structure in which two sheets of the implant material 15 are piled up and a layer form porous article 1 is interposed between them.

Figure 16:
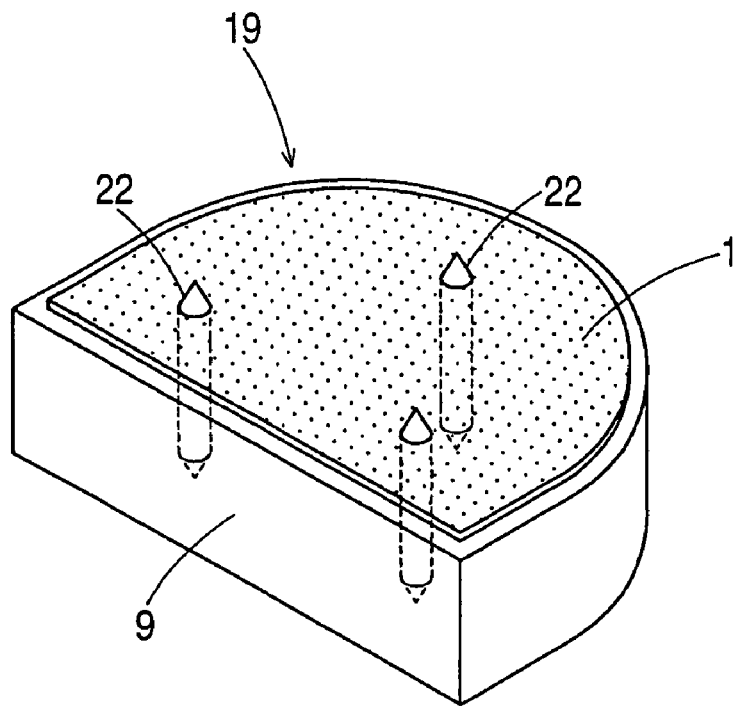
FIG. 16 is a perspective illustration showing still another embodiment of the implant material according to the invention.
Figure 17:
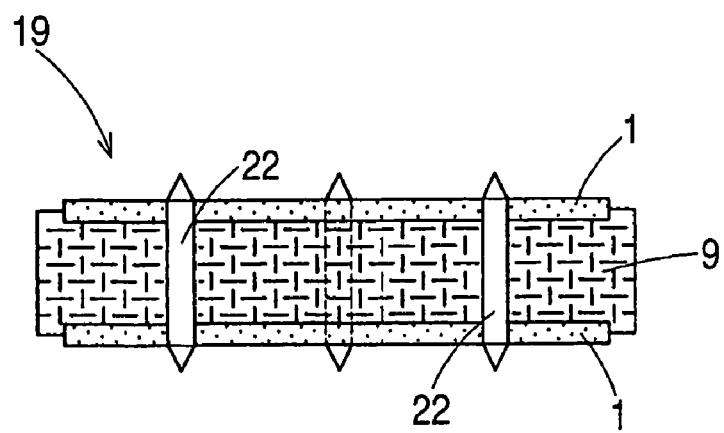
FIG. 17 is a sectional view showing the implant material of the same embodiment.

FIG. 16 and FIG. 17 show an implant material 19 for artificial cartilage use. This implant material 19 for artificial cartilage use has the aforementioned organic-inorganic complex porous article 1, a core material 9 as a bio-non-absorbable member and a pin 22 for fixing use as a biodegradable and bioabsorbable member, in which a porous article 1 is laminated and united on both upper and lower sides of the bio-non-absorbable core material 9, and the tip of the pin 22 for fixing use is protruded from the surface of the porous article 1.

This implant material 19 for artificial cartilage use is formed into a block shape having a flat shape which is roughly square at the head and round at the foot as a result of uniting a rectangle with a half circle as shown in FIG. 16, and is suitably used as an artificial intervertebral disk.

The core material 9 comprises a texture structure body in which organic fibers are made into a three dimensional woven texture or knitted texture or a complex texture thereof and has mechanical strength and flexibility similar to those of intervertebral disk or the like cartilage, and its deformation is markedly biomimetic (living body mimicry). The texture structure body of this core material 9 is similar to the texture structure body described in Japanese Patent Application No. Hei.-6-254515 already applied by the present applicant, and when its geometrical shape is represented by the number of dimensions and the number of its fiber arrangement directions is represented by the number of axes, a structural body comprising a multiaxis-three dimensional texture of three axes or more is suitably employed.

The three axes-three dimensional texture is a product in which fibers in lengthwise, breadthwise and vertical three axis directions are woven or knitted three-dimensionally, and the typical shape of the structural body is a bulk form having a thickness (plate form or block form) like the case of the aforementioned core material 9, but it is possible to make into a cylindrical shape or honeycomb shape. Based on the difference in textures, this three axes-three dimensional texture is classified into an orthogonal texture, a non-orthogonal texture, a leno texture, a cylindrical texture and the like. Also, regarding a structural body of a multiaxis-three dimensional texture of four axes or more, isotropy in strength of the structural body can be improved by arranging 4, 5, 6, 7, 9, 11 axes and the like multiple axis directions. By selecting these conditions, a core material which is more biomimetic and more closely resembled to the cartilage tissues of the living body can be obtained.

It is desirable that porosity of the inner moiety of the core material 9 comprising the aforementioned texture structure body is within the range of from 20 to 90%, because when it is less than 20%, the core material 9 becomes compact to spoil its flexibility and deforming property and therefore becomes unsatisfactory as the core material of an implant material for artificial cartilage, and when it exceeds 90%, compressive strength and shape keeping property of the core material 9 are reduced so that it is unsuitable as the core material of an implant material for artificial cartilage.

As the organic fibers which constitute the core material 9, bio-inactive synthetic resin fibers such as fibers of polyethylene, polypropylene, polytetrafluoroethylene and the like, coated fibers bio-inactivated by coating organic core fibers with the aforementioned bio-inactive resin, and the like are preferably used. Particularly, coated fibers having a diameter of approximately from 0.2 to 0.5 mm, prepared by coating core fibers (twine) of an ultra-high molecular weight polyethylene with the coating of a straight chain low density polyethylene, are the most appropriate fibers in view of strength, hardness, flexibility, easy weaving and knitting and the like. Alternatively, fibers having bioactivity (e.g., having bone conduction or induction ability) can also be selected.

In this connection, the texture structure body constituting the core material 9 is disclosed in detail in the aforementioned Japanese Patent Application No. Hei.-6-254515, so that descriptions further than this are omitted.

The porous article 1 to be laminated on both upper and lower sides of the core material 9 is the same as the aforementioned organic-inorganic complex porous article, namely a biodegradable and bioabsorbable porous article having continuous pores, in which a bioactive bioceramics powder is substantially uniformly dispersed in a biodegradable and bioabsorbable polymer, wherein a part of the bioceramics powder is exposed to the inner face of the pores or the inner face of the pores and the porous article surface. This porous article 1 is prepared by the aforementioned production method of the invention, and its porosity, pore size of the continuous pores, ratio of the continuous pores occupying the total pores, the biodegradable and bioabsorbable polymer, the bioceramics powder, percentage content of said powder and the like are as described in the foregoing.

Since this porous article 1 has a role as a spacer, when this porous article 1 is laminated on both sides of the core material 9 and when this implant material 16 is inserted between cervical vertebrae, lumbar vertebrae or the like vertebral bodies (cf. cervical vertebrae $C_3$ and $C_4$ or lumbar vertebrae $L_4$ and $L_5$ in FIG. 6), the porous article 1 is compression-deformed by the clipping pressure of the upper and lower vertebral bodies and closely contacted with the vertebral bodies without a gap, and accompanied by the hydrolysis of the porous article 1 due to its contact with humors, a bone tissue is conducted and formed in the inner portion of the porous article 1 by the bone conduction ability of the bioceramics powder, and the porous article 1 is replaced by the bone tissue within a relatively short period of time, and the vertebral bodies and the core material 9 are directly bonded. In this case, when the surface layer is bio-activated by spraying a bioceramics powder to the surface of the core material 9, the conducted living bone binds to this activated surface layer, so that direct bonding of the vertebral bodies and the core material 9 is effected within a relatively short period of time and the strength is also maintained. In addition, when a bone induction factor is contained in this porous article 1, bone induction is exhibited so that it is more effective.

It is desirable to set thickness of this porous article 1 to approximately from 0.5 to 3 mm, because when it is thinner than 0.5 mm, it becomes difficult to absorb irregularity on the surface of the vertebral bodies due to compression deformation so that there is a possibility of reducing closely contacted property with the vertebral bodies, and when thicker than 3 mm on the other hand, the period of time required for the degradation and absorption and substitution with a bone tissue becomes long. Also, as shown in FIG. 17, it is desirable to laminate this porous article 1 in such a manner that about half of its thickness is buried in the core material 9 and thereby to surround the porous article 1 with the peripheral part of the core material 9, because abrasion of the periphery of the porous article 1 can be inhibited by such an arrangement.

In this connection, appropriate amounts of the aforementioned ossification factors, growth factors, drugs and the like may be contained in this porous article 1, and in that case, ossification in the inner moiety of the porous article 1 is considerably accelerated and direct binding of the core material 9 with vertebral bodies is established effectively in a early stage. In addition, effects of the penetration and growth of osteoblast to be proliferated may be increased by applying the aforementioned oxidation treatment to the surface of the porous article 1 and thereby improving its wettability.

The fixing pin 22 passes through the aforementioned core material 9 and porous articles 1 on both sides thereof, and both termini of the pin are projected from the porous articles 1. In case that such a fixing pin 22 is present, when this implant material 19 is inserted between upper and lower vertebral bodies, both termini of the fixing pin 22 projecting from the porous articles 1 cut into the contacting faces of the vertebral bodies by the clipping pressure of the upper and lower vertebral bodies, so that the implant material 19 is fixed between the vertebral bodies and does not generate misplacement.

It is desirable that the number of the fixing pin 22 is two or more, most preferably 3 as shown in the drawing, and in that case, there is an advantage in that this material can be stably installed between the upper and lower vertebral bodies effected by the three-point support. It is desirable to form both termini of the fixing pin 22 into a conical or the like pointed shape, and it is desirable to set diameter of the pin 22 to approximately from 1 to 3 mm in order to ensure its strength. In addition, it is desirable to set the projecting size of both termini of the fixing pin 22 to approximately from 0.3 to 2 mm.

Since a large clipping pressure is applied to the fixing pin 22 from the upper and lower vertebral bodies at the beginning when the implant material 19 is inserted between the vertebral bodies, a fixing pin having large strength is required. Accordingly, it is desirable to produce this fixing pin 22 using crystalline polylactic acid, polyglycolic acid and the like biodegradable and bioabsorbable polymers having a viscosity average molecular weight of 150,000 or more, preferably approximately from 200,000 to 600,000, and the use of these polymers further mixed with a bioactive bioceramics powder is also desirable. In addition, as occasion demands, the strength may be improved through the orientation of polymer molecules by compression molding, forged molding, stretching or the like method.

When the implant material 19 for artificial cartilage of the aforementioned construction is installed as an artificial intervertebral disk between upper and lower vertebral bodies, both termini of the fixing pin 22 projecting from the surface of the porous articles 1 cut into the contacting faces of the vertebral bodies as already described in the foregoing, so that the implant material 19 is fixed between the vertebral bodies and does not generate displacement. Accordingly, since fixation of living body materials using auxiliary fixing tools and the like becomes unnecessary, operations can be carried out easily. In addition, when the implant material 19 is installed between vertebral bodies in this manner, the porous article 1 on the surface of the core material 9 is compressed by the clipping pressure of the upper and lower vertebral bodies and closely contacted with the vertebral bodies without a gap, and as degradation and absorption of the porous article 1 advance, a bone tissue is conducted and formed in the inner portion of the porous article 1, so that the porous article 1 is replaced by the bone tissue within a relatively short period of time and the vertebral bodies and the core material 9 are directly bonded. However, since the core material 9 is a bio-inactive synthetic resin fiber, the bone tissue is not conducted and formed inside thereof, and it keeps its flexibility. Since this core material 9 comprises a texture structure body prepared by converting organic fibers into a multi-axial three dimensional weave texture or knit texture of three axes or more or a complex texture thereof as already described, it has mechanical strength and flexibility similar to those of intervertebral disk or the like cartilage, and its deformation is relatively easy, so that it can perform a role of the intervertebral disk showing almost the same behavior of the intervertebral disk. In addition, the fixing pin 22 is also degraded and absorbed by the living body within a relatively short period of time so that it does not remain.

As described in the above, regarding this implant material 19 for artificial cartilage, the core material 9 is biomimetic and its behavior closely resembles cartilage tissues, and in addition to this, it has direct binding ability with and early stage independence from vertebral body and the like bone end-plates, its own side slip and rolling is prevented by the tip of the fixing pin 22 stuck into the bone tissue, and the porous article 1 binds to directly to the bone tissue and histologically integrated into one body. Accordingly, this implant material 19 for artificial cartilage can dissolve all of the already described disadvantages involved in the conventional independent type artificial intervertebral disk of sandwich structure.

In this connection, in the aforementioned implant material 19 for artificial cartilage, the porous article 1 is laminated on both sides of the core material 9 and both termini of the fixing pin 22 are protruded from the porous article 1, it may be made into a construction in which the porous article 1 is laminated on one side of the core material 9 and one side tip of the fixing pin 22 is protruded. Since an implant material for artificial cartilage of such a construction can fix its one side to one of the vertebral bodies with the fixing pin 22, the fixing strength is reduced but displacement of the implant material 19 can be prevented. Also, thickness of the porous article 1 may be increased gradually from its square head part toward round foot part, and when arranged in this manner, the space between the upper and lower vertebral bodies becomes slightly narrow in the head side and slightly broad in the foot side so that it becomes an implant material which can be installed by exactly fitting to said space. In addition, as occasion demands, instead of the fixing pin 22 to be passed through, a short fixing pin may be embedded into the surface layer region of the core material 9 and the pin tip may be protruded from the porous article 1.

Thus, an implant material 19 for artificial intervertebral disk has been described, but it goes without saying that it becomes implant materials for semilunar disk and various types of joint cartilage other than the artificial intervertebral disk when its shape is optionally changed.

While the invention has been described in detail and with reference to specific embodiments thereof, it will be apparent to one skilled in the art that various changes and modifications can be made therein without departing from the spirit and scope of the invention.

This application is based on Japanese patent application filed on Nov. 27, 2001 (Japanese Patent Application No. 2001-360766), Japanese patent application filed on Dec. 3, 2001 (Japanese Patent Application No. 2001-368558), Japanese patent application filed on Feb. 20, 2002 (Japanese Patent Application No. 2002-043137), Japanese patent application filed on Aug. 23, 2002 (Japanese Patent Application No. 2002-242800) and Japanese patent application filed on Sep. 30, 2002 (Japanese Patent Application No. 2002-285934), the entire contents thereof being hereby incorporated by reference.

INDUSTRIAL APPLICABILITY

The implant material of the invention is practically used as a scaffolding for the reconstruction of living bone tissue, a prosthetic material, a bone filler, an inclusion between other implant and a living bone tissue, a substitute for spongy bone, a carrier for sustained drug release and the like. Also, by uniting with other biodegradable and bioabsorbable member and/or bio-non-absorbable member, the implant material of the invention is practically used as various bone fixing materials, a vertebral body fixing material, various spacers between living bones, a defect bone part filling material, a prosthetic material or filler, an artificial cartilage material and the like.

The invention claimed is:

1. An implant material comprising a bioactive organic-inorganic complex porous article which is a biodegradable and bioabsorbable bioactive porous article in which a bioactive bioceramics powder is uniformly dispersed in a biodegradable and bioabsorbable polymer, wherein the bioactive organic-inorganic complex porous article is obtained by forming a nonwoven fabric-like fiber aggregate from a mixed solution of a biodegradable and bioabsorbable polymer and a bioactive bioceramics powder, forming the nonwoven fabric-like fiber aggregate into a porous fiber aggregate molding by compression-molding under heating, soaking the fiber aggregate molding in a volatile solvent, and then removing said solvent, wherein the mixed solution is prepared by dissolving a biodegradable and bioabsorbable polymer in a volatile solvent and dispersing a bioactive bioceramics powder in the resulting solution.

2. The implant material described in claim 1, wherein porosity of the porous article is from 50 to 90%, and the continuous pores occupy from 50 to 90% of the total pores.

3. The implant material described in claim 1, wherein the pore size of the continuous pores of the aforementioned porous article is approximately from 100 to 400 μm.

4. The implant material described in claim 1, wherein the biodegradable and bioabsorbable polymer of the porous article is any one of a totally absorbable poly-D,L-lactic acid, a block copolymer of L-lactic acid with D,L-lactic acid, a copolymer of lactic acid with glycolic acid, a copolymer of lactic acid with p-dioxanone and a block copolymer of lactic acid with ethylene glycol.

5. The implant material described in claim 1, wherein the percentage content of bioceramics powder of the porous article is from 60 to 90% by weight.

6. The implant material described in claim 1, wherein the percentage content of bioceramics powder of the porous article is from 50 to 85% by volume.

7. The implant material described in claim 1, wherein an average particle size of the bioceramics powder contained in the porous article is from 0.2 to 10.

8. The implant material described in claim 1, wherein the bioceramics powder contained in the porous article is any one of powders of totally absorbable un-calcined or un-sintered hydroxyapatite, dicalcium phosphate, tricalcium phosphate, tetracalcium phosphate, octacalcium phosphate, calcite, ceravital, diopside and natural coral.

9. The implant material described in claim 1, wherein compressive strength of the porous article is from 1 to 5 MPa.

10. The implant material described in claim 1, wherein an oxidation treatment is applied to the porous article.

11. The implant material described in claim 1, wherein the porous article has a three dimensional solid shape having a thickness of from 1 to 50 mm.

12. A method for producing an implant material comprising an organic-inorganic complex porous article of claim 1, comprising
    (a) dissolving a biodegradable and bioabsorbable polymer in a volatile solvent and dispersing a bioactive bioceramics powder therein to form a mixed solution,
    (b) forming a nonwoven fabric-like fiber aggregate from the mixed solution,
    (c) compression-molding the nonwoven fabric-like fiber aggregate under heat to form a porous fiber aggregate molding,
    (d) soaking the porous fiber aggregate molding in the volatile solvent, and
    (e) removing the solvent, thereby producing an implant material comprising an organic-inorganic complex porous article.

13. The method described in claim 12, wherein the compression-molding of (c) comprises two steps: (i) solidifying the nonwoven fabric-like fiber aggregate under heating and compression to prepare a preliminarily molded product, and (ii) subjecting the preliminarily molded product to compression molding under a pressure higher than the pressure used to prepare the preliminarily molded product, thereby preparing the porous fiber aggregate molding.

14. The production method described in claim 12, wherein in the soaking of (d), the porous fiber aggregate molding is packed in a mold having a predetermined shape and a large number of pores prior to exposure to the solvent, and soaked in the solvent while maintaining the shape of the mold.

* * * * *